US010758607B2

(12) United States Patent
Peeples et al.

(10) Patent No.: US 10,758,607 B2
(45) Date of Patent: Sep. 1, 2020

(54) RESPIRATORY SYNCYTIAL VIRUS HAVING CLEAVAGE-RESISTANT G PROTEIN AND RELATED MATERIALS AND METHODS

(71) Applicant: The Research Institute at Nationwide Children's Hospital, Columbus, OH (US)

(72) Inventors: Mark Edward Peeples, Bexley, OH (US); Steven A. Kwilas, Fort Detrick, MD (US); Jacqueline Dianne Corry, Columbus, OH (US)

(73) Assignee: The Research Institute at Nationwide Children's Hospital, Columbus, OH (US)

( * ) Notice: Subject to any disclaimer, the term of this patent is extended or adjusted under 35 U.S.C. 154(b) by 0 days.

(21) Appl. No.: 15/737,225

(22) PCT Filed: Jun. 17, 2016

(86) PCT No.: PCT/US2016/038068
§ 371 (c)(1),
(2) Date: Dec. 15, 2017

(87) PCT Pub. No.: WO2016/205641
PCT Pub. Date: Dec. 22, 2016

(65) Prior Publication Data
US 2019/0083600 A1    Mar. 21, 2019

Related U.S. Application Data

(60) Provisional application No. 62/181,075, filed on Jun. 17, 2015.

(51) Int. Cl.
*A61K 39/12* (2006.01)
*C07K 14/005* (2006.01)
*A61K 39/00* (2006.01)

(52) U.S. Cl.
CPC ............ *A61K 39/12* (2013.01); *C07K 14/005* (2013.01); *A61K 2039/525* (2013.01); *A61K 2039/545* (2013.01); *C12N 2760/18522* (2013.01); *C12N 2760/18534* (2013.01)

(58) Field of Classification Search
None
See application file for complete search history.

(56) References Cited

U.S. PATENT DOCUMENTS

2006/0171955 A1   8/2006   Alonso-Caplen et al.
2011/0135680 A1   6/2011   Song et al.
2015/0150878 A1   6/2015   Prabhakar et al.

FOREIGN PATENT DOCUMENTS

WO       2014/170257 A1      10/2014

OTHER PUBLICATIONS

Corry et al., J Virology 2016, vol. 90, pp. 1311-1320 (Year: 2016).*
Johnson et al. PNAS vol. 84, pp. 5625-5629 (Year: 1987).*
Kwilas et al. JV 2009 vol. 83, pp. 10710-10718 (Year: 2009).*
International Search Report and Written Opinion issued in PCT/US16/38068, dated Jan. 10, 2017, 14 pages.
Kwilas, S et al. 'Respiratory Syncytial Virus Grown in Vero Cells Contains a Truncated Attachment Protein That Alters Its infectivity and Dependence on Glycosaminoglycans' Journal of virology, 2009, vol. 83, No. 20, pp. 10710-10718; abstract. DOI:10.1128/JVI.00986-09.
Balmaks, R et al. 'Molecular Epidemiology of Human Respiratory Syncytial Virus Over Three Consecutive Seasons in Latvia' Journal of medical virology, 2014, vol. 86, No. 11, pp. 1971-1982; p. 1974, first column, second paragraph; figure 3a. DOI 10.1002/jmv.23855.

* cited by examiner

*Primary Examiner* — Shanon A. Foley
*Assistant Examiner* — Myron G Hill
(74) *Attorney, Agent, or Firm* — Faegre Drinker Biddle & Reath LLP

(57) ABSTRACT

Embodiments disclosed herein provide compositions, methods, and uses for respiratory syncytial viruses (RSV) and immunogenic compositions thereof. Certain embodiments provide RSV having cleavage-resistant mutated attachment (G) glycoproteins. In some embodiments, the cleavage-resistant G protein mutants increase production of live attenuated RSV in host cells. Also provided are methods for amplifying RSV in host cells, wherein the amplified RSV has full length G protein. In certain embodiments, the amplified RSV having full length G protein is formulated into immunogenic compositions, including vaccines. Other embodiments provide methods for inducing an effective immune response against RSV infection in a subject.

26 Claims, 8 Drawing Sheets
Specification includes a Sequence Listing.

|            | VeD |   | rgRSV |   |
|------------|-----|---|-------|---|
| Cath L inh | −   | + | −     | + |
| Cath L     | −   | − | +     | + |

SEQUENCE LISTING

<160> NUMBER OF SEQ ID NOS: 8

<210> SEQ ID NO 1
<211> LENGTH: 298
<212> TYPE: PRT
<213> ORGANISM: Human respiratory syncytial virus

<400> SEQUENCE: 1

```
Met Ser Lys Asn Lys Asp Gln Arg Thr Ala Lys Thr Leu Glu Arg Thr
 1               5                  10                  15

Trp Asp Thr Leu Asn His Leu Leu Phe Ile Ser Ser Cys Leu Tyr Lys
                20                  25                  30

Leu Asn Leu Lys Ser Val Ala Gln Ile Thr Leu Ser Ile Leu Ala Met
            35                  40                  45

Ile Ile Ser Thr Ser Leu Ile Ile Ala Ala Ile Ile Phe Ile Ala Ser
50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Gln Thr Gln Pro Ser
130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
    290                 295
```

<210> SEQ ID NO 2
<211> LENGTH: 16
<212> TYPE: DNA
<213> ORGANISM: Artificial Sequence
<220> FEATURE:
<223> OTHER INFORMATION: Synthetic primer -continued

```
<400> SEQUENCE: 2
gggacggctg taatgg                                                             16

<210> SEQ ID NO 3
<211> LENGTH: 19
<212> TYPE: DNA
<213> ORGANISM: Artificial Sequence
<220> FEATURE:
<223> OTHER INFORMATION: Synthetic primer

<400> SEQUENCE: 3
ttggtacact cctgacttg                                                          19

<210> SEQ ID NO 4
<211> LENGTH: 18
<212> TYPE: DNA
<213> ORGANISM: Artificial Sequence
<220> FEATURE:
<223> OTHER INFORMATION: Synthetic primer

<400> SEQUENCE: 4
gaggcaacag aagaatcc                                                           18

<210> SEQ ID NO 5
<211> LENGTH: 17
<212> TYPE: DNA
<213> ORGANISM: Artificial Sequence
<220> FEATURE:
<223> OTHER INFORMATION: Synthetic primer

<400> SEQUENCE: 5
cccagctgtt cttcacc                                                            17

<210> SEQ ID NO 6
<211> LENGTH: 7
<212> TYPE: PRT
<213> ORGANISM: Artificial Sequence
<220> FEATURE:
<223> OTHER INFORMATION: derived from human respiratory syncytial virus
      G protein
<220> FEATURE:
<221> NAME/KEY: MISC_FEATURE
<222> LOCATION: (3)..(4)
<223> OTHER INFORMATION: Xaa can be any naturally occuring amino acid

<400> SEQUENCE: 6

Leu Lys Xaa Xaa Lys Lys Asp
1               5

<210> SEQ ID NO 7
<211> LENGTH: 298
<212> TYPE: PRT
<213> ORGANISM: Artificial sequence
<220> FEATURE:
<223> OTHER INFORMATION: synthetic sequence based on human respiratory
      syncytial virus G protein
<220> FEATURE:
<221> NAME/KEY: MISC_FEATURE
<222> LOCATION: (208)..(208)
<223> OTHER INFORMATION: Xaa can be any naturally occurring amino acid
      other than Leu
<220> FEATURE:
<221> NAME/KEY: MISC_FEATURE
<222> LOCATION: (209)..(209)
<223> OTHER INFORMATION: Xaa can be any naturally occurring amino acid
      other than Lys
<220> FEATURE:
<221> NAME/KEY: MISC_FEATURE
```

<222> LOCATION: (212)..(213)
<223> OTHER INFORMATION: Xaa can be any naturally occurring amino acid
      other than Lys
<220> FEATURE:
<221> NAME/KEY: MISC_FEATURE
<222> LOCATION: (214)..(214)
<223> OTHER INFORMATION: Xaa can be any naturally occurring amino acid
      other than Asp

<400> SEQUENCE: 7

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Xaa
        195                 200                 205

Xaa Thr Thr Xaa Xaa Xaa Pro Lys Pro Gln Thr Thr Lys Ser Lys Glu
210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
    290                 295

<210> SEQ ID NO 8
<211> LENGTH: 298
<212> TYPE: PRT
<213> ORGANISM: Artificial sequence
<220> FEATURE:
<223> OTHER INFORMATION: Human respiratory syncytial virus G protein
      having an L to A mutation at amino acid 208

<400> SEQUENCE: 8

```
Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
            35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Ala
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
            275                 280                 285

Pro Ser Ser Pro Pro Asn Thr Pro Arg Gln
290                 295
```

RESPIRATORY SYNCYTIAL VIRUS HAVING CLEAVAGE-RESISTANT G PROTEIN AND RELATED MATERIALS AND METHODS

CROSS REFERENCE TO RELATED APPLICATIONS

This application is a U.S. National Stage Application under 35 U.S.C § 371 of International Application No. PCT/US2016/038068, filed on Jun. 17, 2016, which claims the benefit of U.S. Provisional Patent Application No. 62/181,075, filed on Jun. 17, 2015, the disclosures of each of which are, incorporated herein by reference in their entireties.

STATEMENT REGARDING FEDERALLY SPONSORED RESEARCH

This invention was made with government support under Grant No. AI093848 awarded by the National Institutes of Health. The government has certain rights in the invention.

SEQUENCE LISTING

The instant application contains a Sequence Listing which has been submitted via EFS-web in ASCII format and is hereby incorporated by reference in its entirety. The ASCII copy, created on Jun. 12, 2016, is named 509892.9_SequenceListing_ST25, and is 10,352 bytes in size. A substitute sequence listing was submitted via EFS-web in ASCII format and is hereby incorporated by reference in its entirety. The substitute ASCII file, created on Nov. 28, 2018, is named 509892.13_SubstituteSequenceListing_ST25.txt, and is 10,018 bytes in size.

FIELD

Embodiments disclosed herein provide compositions, methods, and uses for respiratory syncytial viruses (RSV) and immunogenic compositions thereof. Certain embodiments concern respiratory syncytial viruses (RSV) having cleavage-resistant mutated attachment (G) glycoproteins. In some embodiments, cleavage-resistant G protein mutants can increase production of live RSV in host cells. Other embodiments provide methods for amplifying RSV in host cells, where the amplified RSV has full length G proteins. In certain embodiments, the amplified RSV having full length G proteins can be formulated into immunogenic compositions, for example, of use as vaccines against RSV. Other embodiments provide compositions for use in methods for inducing an effective immune response against RSV infection in a subject.

BACKGROUND

First discovered in 1956 as a lower respiratory tract pathogen of children in their first year of life, human respiratory syncytial virus (RSV) is an enveloped, negative-sense single-stranded RNA virus belonging to the *Pneumovirus* genus within the Pneumovirinae subfamily of the family Paramyxoviridae. RSV is a major cause of lower respiratory tract infections, most commonly resulting in mild respiratory tract disease. However, infection with hRSV may result in severe bronchiolitis and pneumonia. In industrialized countries, RSV accounts for up to 70% of hospitalized bronchiolitis cases. Among infectious agents, respiratory syncytial virus is the second leading cause of death in infants. Worldwide, in 2010 alone, RSV is estimated to have caused over 230,000 deaths in children under 5 years of age, with the majority of deaths being in infants under the age of one (Lozano et al., Lancet (2012.) 380:2095-2128).

Currently, only supportive care is available to treat subjects infected with lower respiratory tract disease. In certain cases, a humanized neutralizing monoclonal antibody (mAb), palivizumab, can be used prophylactically, but is typically only used on infants considered at greatest risk for severe disease.

In the 1960s, a formalin-inactivated RSV vaccine was tested in infants and young children. Instead of protecting the airways of the infants upon natural infection, 80% of the vaccinated infants were hospitalized and two infants succumbed, while only 5% of the control vaccinated infants were hospitalized (Kim et al., Am J Epidemiol (1969) 89:422-434). As a result, the focus shifted to live, attenuated viral vaccines for protection and a great deal of effort has been spent developing these vaccines (Crowe et al., Vaccine (1995) 13:847-855; Karron et al., J Infect Dis (2005) 191: 1093-1104; Karron et al., J Infect Dis (1997) 176:1428-1436; Kim et al., Pediatrics (1971) 48:745-755; Malkin et al., PLoS One (2013) 8:e77104; Wright et al., J Infect Dis (2000) 182:1331-1342; Wright et al., J Infect Dis (2006) 193:573-581).

SUMMARY

Embodiments disclosed herein provide compositions, methods, and uses for respiratory syncytial viruses (RSV) and immunogenic compositions thereof. Certain embodiments provide RSV having cleavage-resistant mutated attachment (G) glycoproteins. In some embodiments, the cleavage-resistant G protein mutants increase production of live RSV in host cells. In other embodiments, methods for amplifying RSV in host cells are disclosed, wherein the amplified RSV has full length G protein. In certain embodiments, the amplified RSV having full length G protein can be formulated into an immunogenic composition against RSV, for example, a vaccine for reducing or preventing RSV infection. Other embodiments provide compositions for use in methods for inducing an effective immune response against RSV infection in a subject.

In some embodiments, a modified RSV can have a mutated G protein that is more resistant to protease cleavage than a control G protein. In accordance with these embodiments, the mutated G protein can be more resistant to protease cleavage. In other embodiments, the mutated G protein of an RSV can be more resistant to cleavage when grown in Vero cells, providing improved growth of the virus. In certain embodiments, the mutated G protein can be more resistant to cleavage by cathepsin L. In some embodiments, the G protein is mutated relative to a G protein represented by the polypeptide sequence of SEQ ID NO: 1. In some embodiments, the G protein can have a mutation where the amino acid of the G protein is changed to a different amino acid to increase resistance to protease cleavage. In accordance with these embodiments, one mutation in the G protein can be an amino acid substitution or mutation in the polynucleotide to render at least one amino acid change in the G protein polypeptide. For example, the G protein can have at least one amino acid substitution including, but not limited to, an amino acid substitution at least at one or more of L208, K209, K12, and D214. In other embodiments, an amino acid substitution of the G protein can be at L208, K209, or a combination of amino acids L208 and K209.

In some embodiments, one or more G protein amino acids can be substituted for another amino acid, where the substitution is capable of conferring cleavage resistance to the RSV G protein. In other embodiments, the substituted amino acid can be any hydrophobic amino acid, for example, alanine, valine, leucine, isoleucine, proline, phenylalanine, tryptophan, cysteine, tyrosine, and methionine. In yet other embodiments, the substitutable amino acid can be replaced by alanine.

In other embodiments, an RSV G protein can have a deletion mutation that confers cleavage resistance to the mutated G protein. In some embodiments, at least one of L208, K209, T210, and T211 is deleted. In some embodiments, the mutated G protein can be resistant to cleavage when the RSV having the mutated G protein is grown in Vero cells. In other embodiments, the mutated G protein can be resistant to cleavage by cathepsin L.

In other embodiments, a nucleic acid sequence encoding an RSV having a G protein that is more resistant to protease cleavage than a control G protein is provided. In other embodiments, an RSV having a mutated G protein that is more resistant to protease cleavage than a control G protein can be an attenuated RSV virus.

Certain embodiments provide methods for producing an immunogenic composition against RSV where the immunogenic composition can include, but is not limited to, an RSV having a mutated G protein. In other embodiments, methods can include having a host cell culture and inoculating the host cell culture with an RSV described herein having a mutated G protein that is more resistant to protease cleavage than a control G protein, incubating the host cell culture with the RSV, harvesting the RSV from the host cell culture following a period of incubation, and formulating the harvested RSV into an immunogenic composition of use against RSV infection. Some embodiments can further include purifying the harvested RSV.

In some embodiments, methods disclosed herein can include methods for generating an RSV having a full-length G protein. In certain embodiments, the G protein is a protease resistant G protein. In other embodiments, reducing protease cleavage of the targeted RSV G protein can be attained by incubating inoculated host cells with a protease inhibitor. In some embodiments, cleavage of the RSV G protein is inhibited by incubating the inoculated host cells with one or more protease inhibitors. In some embodiments, the protease inhibitor is removed from harvested virions through a purification step.

In some embodiments, host cells of use in methods disclosed herein can be any cell of use to grow RSV. In other embodiments, host cells of use in compositions and methods disclosed herein can include, but is not limited to, Vero cells.

In other embodiments, targeted protease inhibitors of use herein can include, but are not limited to, cathepsin L inhibitors. In accordance with these embodiments, cathepesin L inhibitors can include, but are not limited to, 3-epiursolic acid, 3-(hydroxyimino)oleanolic acid, 3-(hydroxyimino)masticadienoic acid, ALLM, ALLN, biotin-FA-FMK, CAA0225, CA-074, CA-074 Me, Calpain Inhibitor I, Calpain Inhibitor II, Calpain Inhibitor III, Calpain Inhibitor IV, Calpain Inhibitor V, Calpain Inhibitor VI, Calpeptin, Catfish muscle cathepsin inhibitor, Cathepsin inhibitor peptide, Cathepsin Inhibitor 1, Cathepsin L inhibitor, Cathepsin L inhibitor I, Cathepsin L inhibitor II, Cathepsin L inhibitor III, Cathepsin L inhibitor IV, Cathepsin L inhibitor Katunuma, CLIK148, Cathepsin/subtilisin inhibitor, Chagasin, Chloroketones, Chymostatin, Clitocypin, CTLA-2 alpha, CTLA-2 beta, Cystatins, Disulfiram, E-64, E-64-c, E-64-d, Gallinamide A, Hurpin, KD-1, KGP94, L006235, Leupeptin, L-transepoxysuccinyl-L Leu cylamine, MDL28170, Mu-Phe-hPhe-FMK, N-(1-Napthalenlsulfonyl)-Ile-Trp-aldehyde, N-Acetyl-L-Leucyl-L-Leucyl-L-methional, Napsul-Ile-Trp-CHO (NSITC), Oxocarbazate, Peptidomimetic 2-cyanopyrrolidines, Phenylmethanesulfonyl fluoride, Protein C inhibitor, SID 26681509, Squamous cell carcinoma antigen, Thiocarbazate, Triterpenoids, Z-FA-FMK, Z-FF-FMK, ZINC03846634 (APQ), ZINC08764437 (NFP), Z-Phe-Ala-CHN2, Z-Phe-Phe-CH2F, Z-Phe-Tyr (tBu)-diazomethylketone, Z-Phe-Tyr-aldehyde, α-macroglobulin, or a molecule of WO 2000049008 A1. In some embodiments, the cathepsin L inhibitor can be Leupeptin.

In other embodiments, cleavage of the RSV G protein can be generated using an RNAi. In some embodiments, an RNAi can be generated by one or more molecules selected from siRNA, miRNA, shRNA, or a combination thereof. In certain embodiments, the RNAi targets or binds to and inhibits an mRNA encoding cathepsin L.

In some embodiments, formulating an RSV or RSV having a mutated G protein can include obtaining harvested attenuated RSV and providing a pharmaceutically acceptable carrier, vehicle, or excipient, an adjuvant, or a combination thereof to generate a live, attenuated RSV pharmaceutically acceptable composition.

In other embodiments, inoculated host cells can be incubated with the mutated RSV for about an incubation period of about 30 minutes to about 96 hours. In some embodiments, the inoculated host cells are incubated with the mutated RSV for about 30 minutes to about 4 hours. In some embodiments, the inoculated host cells are incubated with mutated RSV for about 2 hours. In other embodiments, the inoculated host cells are incubated with the mutated RSV for about 48 to 96 hours. In some embodiments, the inoculated host cells are incubated with the mutated RSV for about 72 hours.

In some embodiments, immunogenic compositions against RSV can be formulated into a pharmaceutical composition where the immunogenic composition can include a pharmaceutically acceptable carrier, vehicle, excipient, or combination thereof. In other embodiments, a pharmaceutically acceptable immunogenic composition against RSV can include an adjuvant for further induction of the immune system in a subject when administered.

Other embodiments provide methods for inducing an immune response against RSV infection in a subject. In some embodiments, the methods include administering to the subject an immunologically effective dose of an immunogenic composition against RSV as provided herein. In some embodiments, the subject can be a human. In other embodiments, the subject can be a human infant or child. In other embodiments, an immunogenic composition against RSV can be administered via any route of administration. In accordance with this embodiment, a route of administration can be but is not limited to, intranasal administration, subcutaneous administration, intramuscular administration, intradermal administration, and oral administration. In some embodiments, at least one additional dose of an immunogenic composition against RSV can be administered to the subject.

BRIEF DESCRIPTION OF THE DRAWINGS

FIG. 2C is an immunoblot illustrating RSV virion-associated G protein cleavage prevention in the presence of cathepsin L inhibitor during virus production in Vero cells and the ability of cathepsin L to cleave the full-length virion associated G protein in vitro.

FIG. 4A is a schematic illustrating the furin-released G (frG) construct. Measles virus (MV) cytoplasmic, transmembrane, and partial stalk sequence is followed by a furin cleavage site (fcs), a 6-histidine tag, a Factor X A cleavage site and the ectodomain of the RSV G protein.

FIG. 4B is an immunoblot illustrating only intact frG proteins being released into the medium from HeLa and Vero cells.

FIG. 4C is an immunoblot illustrating decreased cleavage of membrane-bound RSV G protein in the presence of chloroquine.

DEFINITIONS

Figure 1A:
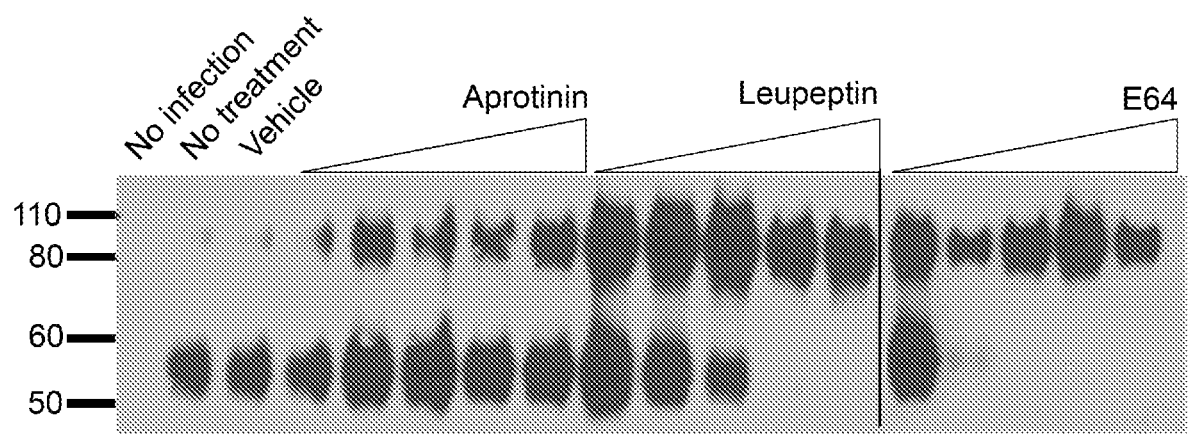
FIG. 1A is an immunoblot representing cleavage of RSV G protein in the presence of general serine protease inhibitor, and prevention of cleavage by the serine/cysteine protease inhibitor Leupeptin and the cysteine protease inhibitor E-64.

So that the disclosure may be more readily understood, certain terms are first defined.

When used in reference to protease cleavage of RSV G protein, the term "resistant" is to be understood to refer to a mutated RSV G protein's ability to reduce or completely eliminate protease cleavage to one or more proteases rendering the RSV G protein resistant to protease cleavage. Therefore, a resistant mutant RSV G protein is an RSV G protein that is present at the cell surface predominantly in its full length (~90 kDa) form.

An "immunogenic composition" refers to any mixture, aqueous, or non-aqueous solution, suspension, emulsion, gel, or the like, including an RSV of an embodiment described herein and other components. RSV can be a live RSV or a live, attenuated RSV. Other components can be, for example, one or more pharmaceutically acceptable agents, carriers, vehicles, excipients, or a combination thereof. Generally, immunogenic compositions can be prepared by uniformly combining the live attenuated virus with a liquid carrier, vehicle, or excipient, or a finely divided solid carrier, vehicle, or excipient, or both. The immunogenic composition includes enough immunogenic virus to induce an effective immune response. Accordingly, the immunogenic compositions described herein encompass any composition made by admixing a compound of mutant RSV described herein or RSV amplified using a method described herein and a pharmaceutically acceptable carrier, vehicle, or excipient. By "pharmaceutically acceptable" it is meant that the carrier, vehicle, or excipient must be compatible with the other ingredients of the formulation and not deleterious to the recipient thereof.

As used herein, the term "effective immune response" refers to an immune response that confers immunity against an infection, treats or ameliorates an existing infection, or reduces the probability of infection recurrence. For instance, an immune response can be considered to be an "effective immune response" if it is sufficient to prevent a subject from developing a respiratory syncytial virus (RSV) infection or a lower respiratory tract RSV infection after administration of a challenge dose of RSV. An effective immune response can include a cell mediated immune response, and/or a humoral immune response.

The term "immunologically effective dose" refers to an amount of a vaccine or vaccine composition of the present disclosure sufficient to cause an effective immune response. The immunologically effective dose can be administered in one or more administration. The precise determination of what would be considered an immunologically effective dose can be based on factors individual to each subject, including but not limited to the subject's age, size, and route of administration.

Numbering of amino acids, unless otherwise specified, is of amino acids comprising the RSV attachment (G) glycoprotein of RSV stain A2 (SEQ ID NO: 1). The first amino acid (from the N-terminus) of RSV G protein is designated amino acid 1. For example, L208 indicates the presence of leucine at amino acid position 208 of the RSV G protein, and the notation L208A indicates the substitution of leucine at position 208 by alanine.

DETAILED DESCRIPTION

In the following sections, various exemplary compositions and methods are described in order to detail various embodiments. It will be obvious to one skilled in the art that practicing the various embodiments does not require the employment of all or even some of the specific details outlined herein, but rather that concentrations, times and other specific details may be modified through routine experimentation. In some embodiments disclosed herein, well known methods or components have not been included in the description.

Embodiments disclosed herein provide compositions, methods, and uses for respiratory syncytial viruses (RSV)

and immunogenic compositions thereof. Certain embodiments provide RSV having cleavage-resistant mutated attachment (G) glycoproteins. In some embodiments, the cleavage-resistant G protein mutants increase production of live RSV in host cells. In other embodiments, methods for amplifying RSV in host cells are disclosed, wherein the amplified RSV has full length G protein. In some embodiments, the amplified RSV having full length G protein can be formulated into an immunogenic composition against RSV, for example, a vaccine for reducing or preventing RSV infection. Other embodiments provide compositions for use in methods for inducing an effective immune response against RSV infection in a subject.

The U.S. Food and Drug Administration has approved production of live, attenuated vaccines in host cell lines MRC-5, WI-38, and Vero. Both MRC-5 and WI-38 cell lines divide much less rapidly than do Vero cells, and produce lower virus yields. In addition, Vero cells do not produce interferon. This can be particularly advantageous for attenuated viruses where the attenuating mutations reduce the ability of the virus to inhibit the interferon response. Such attenuated viruses would be inhibited in their growth during vaccine production in a cell line capable of producing interferon, but not in Vero cells. The higher growth rate of Vero cells, the higher yield of RSV on Vero, and the lack of interferon response in Vero sets this cell line ahead of the other vaccine-producer cell line candidates.

In some embodiments, live, attenuated RSV for use in vaccines have been produced in Vero cells. However, virions produced in Vero cells have reduced infectivity in well-differentiated human airway epithelial (HAE) cultures. Reducing the infectivity of the virus for these primary cells that model the in vivo target cells in the nasal epithelium during inoculation decreases the number of cells infected initially, thereby decreasing the virus's immunogenicity, resulting in significantly greater amounts of an immunogenic composition against RSV being required for administration to a subject to produce a protective immune response. All of these factors increase the economic costs of producing a commercially viable RSV vaccine.

In certain embodiments, the RSV G protein is mutated, resulting in RSV virions having a G protein resistant to protease cleavage. When produced in Vero cells, RSV G protein is normally cleaved, resulting in most of the G protein incorporated into virions being 55 kDa rather that the full-length 90 kDa G. Vero-produced RSV virions are 4-10 fold less infectious in primary HAE cultures than those produced in HeLa cells, having infectivity similar to a virus completely lacking the G protein.

In some embodiments, the mutation in the RSV G protein can be any amino acid mutation resulting in resistance of the G protein to protease cleavage. In some embodiments, the mutated RSV G protein is resistant to cleavage by cathepsin L (see FIGS. 6B-6C). In other embodiments, the mutation in the RSV G protein is relative to the G protein of a wild-type RSV. In some embodiments, the mutation in the RSV G protein is relative to the G protein of RSV strain A2 (SEQ ID NO: 1).

Figure 6A:
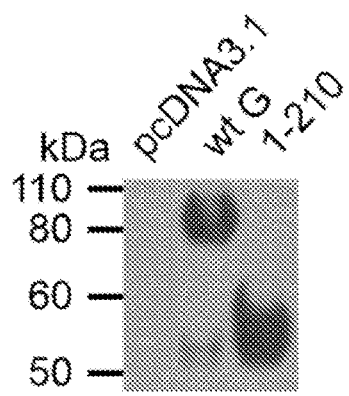
FIG. 6A is an immunoblot illustrating size of a truncated RSV G protein in HeLa cells. A stop codon was inserted at amino acid 211 in the wt G protein gene plasmid.
Figure 6B:
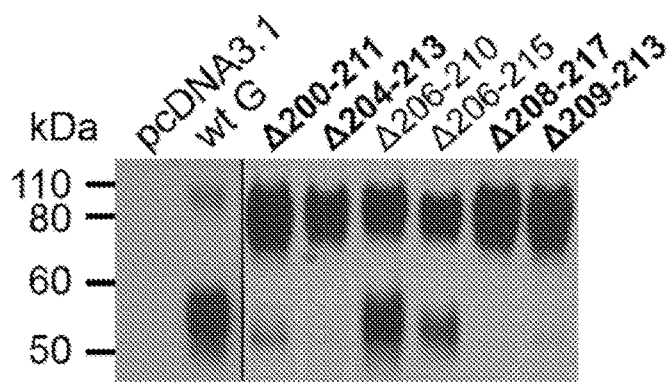
FIG. 6B is an immunoblot illustrating reduced cleavage efficiency in some RSV G protein deletion mutants. The noted overlapping deletion mutations were introduced into the wt G protein gene plasmid.
Figure 6C:
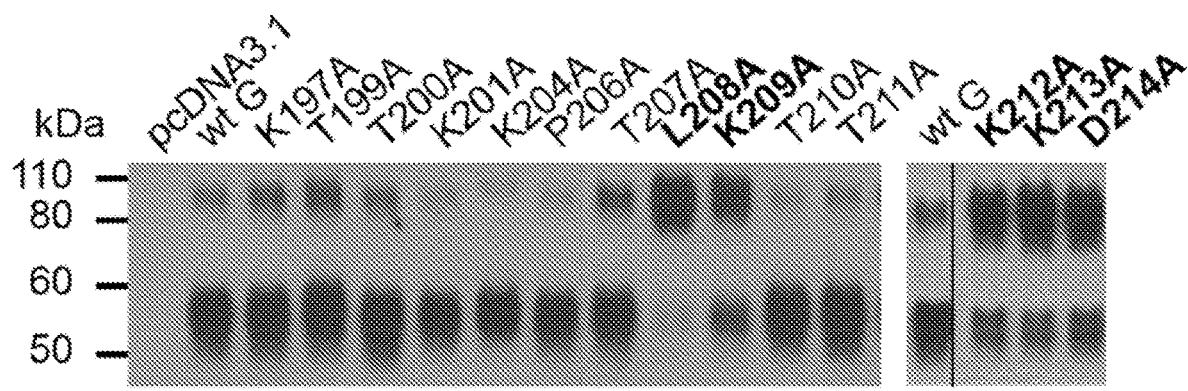
FIG. 6C is an immunoblot illustrating the role of individual amino acids in cleavage of RSV G protein. Amino acids at and around amino acid 210 were mutated separately to alanine.

In some embodiments, mutations in the amino acid sequence of the RSV G protein capable of conferring cleavage resistance to the protein can include, but are not limited, to substitution mutations of amino acids L208, K209, K212, K213, and D214 of SEQ ID NO: 1, and combinations thereof. In a some embodiments, the amino acid sequence of a mutated RSV G protein resistant to cleavage can have a substitution mutation at L208, K209, or both L208 and K209 of SEQ ID NO: 1. In yet another embodiment, the amino acid sequence of a mutated RSV G protein resistant to cleavage can have a substitution mutation at amino acid L208. In some embodiments, the substitution mutation can be the substitution of one or more of amino acids L208, K209, K212, K213 and D214 for any other amino acid. In other embodiments, one or more of amino acids L208, K209, K212, K213 and D214 of SEQ ID NO: 1 are substituted by alanine (see FIG. 6C). In a yet another embodiment, amino acid L208 of the RSV G protein is substituted by alanine (L208A; FIG. 6C).

In some embodiments, the substitution mutation(s) does not affect overall G protein structure or function. In other embodiments, the substitution mutation(s) reduces or prevents cleavage of the RSV G protein by a protease. In certain embodiments, the substitution mutation(s) reduces or prevents cleavage of the RSV G protein by cathepsin L. In yet other embodiments, the substitution mutation(s) does not create an alternative proteolytic site, such as a substitution mutation(s) that results in, for example, consecutive lysine residues.

In some embodiments, an amino acid can be substituted for any other amino acid capable of conferring cleavage resistance to the RSV G protein. In some embodiments, an amino acid to be substituted as described herein can be substituted for any other amino acid. In other embodiments, an amino acid to be substituted can be substituted for any nonpolar or polar hydrophobic amino acid, such as alanine, valine, leucine, isoleucine, proline, phenylalanine, tryptophan, cysteine, tyrosine, and methionine. In yet other embodiments, an amino acid to be substituted can be substituted for alanine.

In other embodiments, mutations in the amino acid sequence of the RSV G protein capable of conferring cleavage resistance to the protein can include, but are not limited, to a deletion mutation of one or more amino acids from about amino acid 198 to about amino acid 218. In certain embodiments, the deletion mutation is a deletion of one or more of L208, K209, K212, K213 and D214 of SEQ ID NO: 1 (FIG. 6B). In some embodiments, the deletion mutation(s) does not affect overall G protein structure or function. In other embodiments, the deletion mutation(s) reduces or prevents cleavage of the RSV G protein by a protease. In yet other embodiments, the deletion mutation(s) reduces or prevents cleavage of the RSV G protein by cathepsin L. In yet other embodiments, the deletion mutation(s) does not result in the creation of an alternative proteolytic site. For example, deletion mutants Δ206-210 and Δ206-215 (SEQ ID NO: 1) bring together amino acids that inhibit but do not abolished protein cleavage (FIG. 6B).

In other embodiments, the amino acid sequence of an RSV G protein having an amino acid sequence different than that provided by SEQ ID NO: 1 is mutated at one or more amino acid positions analogous to those described for SEQ ID NO: 1. For example, in some embodiments, the amino acid sequence of a G protein from an RSV that is not strain A2 can include the amino acid sequence LKXXKKD (SEQ ID NO: 6), which is analogous to amino acids 208 to 214 of SEQ ID NO: 1. In these embodiments, substitution or deletion mutations can be made at position L1, K2, K5, and D7 of SEQ ID NO: 6 (which occurs within a larger G protein amino acid sequence), which are analogous to L208, K209, K212, K213, and D214 of SEQ ID NO: 1, respectively.

Mutations disclosed herein can be achieved by any method known in the art such as, for example, site directed mutagenesis.

In some embodiments, RSV having a G protein resistant to protease cleavage can act as a backbone for attenuating mutations. In other embodiments, a live attenuated RSV virus can be mutated to have a cleavage-resistant G protein as described herein. Live attenuated viruses do not cause vaccine-associated enhanced RSV disease. Rather, they can broadly stimulate innate, humoral, and cellular immunity both systemically and locally in the respiratory tract, they can be delivered intranasally, and they replicate in the upper respiratory tract of young infants despite the presence of passively acquired maternally derived RSV neutralizing antibody. By mutating the RSV G protein as provided by the embodiments described herein and incorporating the cleavage-resistant mutated G protein into a live attenuated RSV, or mutating the RSV G protein of a live attenuated RSV protein to a cleavage-resistant form, live attenuated RSV can be efficiently amplified in Vero cells. In some embodiments, an RSV having a cleavage-resistant G protein grown in Vero cells is up to 10-fold more infectious on HAE cultures than wild-type G protein grown in Vero cells. This allows for reduced inoculum to be used to achieve an effective immune response in a subject. In other embodiments, live attenuated RSV virions having cleavage-resistant G proteins can reduce the volume of inoculum required for immunization with a live attenuated RSV by 4- to 10-fold. This reduction in required inoculum volume can make production of immunogenic compositions including live attenuated RSV, such as vaccines, more economical, and can reduce the amount of viral protein antigens and any cell culture contaminants carried in the inoculum.

In certain embodiments, a live attenuated RSV is modified to incorporated a mutation of the G protein as provided by the embodiments described herein. The G protein of any live attenuated RSV can be so mutated. For example, the G protein of RSV ΔNS2 Δ1313 I1314L, Lot RSV #005A, RSV LID ΔM2-2, and MEDI-559, which are in clinical trials as vaccines, can be modified to improve viral amplification in host cells. It is contemplated herein that any other live attenuated RSV can be mutated as described herein. In certain embodiments, modification of the G protein of a live attenuated RSV as described herein can improve the production of infectious live attenuated RSV virions in Vero cells relative to live attenuated RSV not having the modified G protein.

In other embodiments, an RSV having a mutated and cleavage-resistant G protein can be further modified so as to attenuate the virus and produce a live attenuated RSV with a cleavage-resistant G protein. Any attenuating mutation can be incorporated into the RSV having a mutated and cleavage resistant G protein. Attenuating mutations can include, but are not limited to, those mutations found in RSV ΔNS2 Δ1313 I1314L, RSV cps2, Lot RSV #005A, RSV LID ΔM2-2, and MEDI-559.

In certain embodiments, RSV amplification in Vero cells is improved by inhibiting RSV G protein cleavage during amplification. Improvement is relative to RSV amplified in Vero cells where RSV G protein cleavage is not inhibited. In some embodiments, RSV G protein cleavage is inhibited by mutating the RSV G protein as described herein. In other embodiments, RSV G protein cleavage is inhibited by amplifying RSV not having a G protein mutated as described herein in the presence of one or more protease inhibitors. In yet other embodiments, RSV G protein cleavage is inhibited by mutating the RSV G protein as described herein, and amplifying the RSV having the mutated G protein in the presence of one or more protease inhibitors.

Certain embodiments provide methods for amplifying an RSV. Methods for amplifying an RSV can include providing a cell culture of Vero cells, inoculating the cell culture of Vero cells with an RSV having a cleavage-resistant G protein as described herein, incubating the cell culture with the RSV, and harvesting RSV virus following the incubation period. In some embodiments, the RSV having a cleavage-resistant G protein as described herein is a live attenuated RSV. General parameters for growing Vero cells and amplification of RSV in Vero cells are described below, including throughout the Examples. Routine modifications to adapt these methods to a situation are within the scope of the present disclosure (e.g., cell culture conditions, inoculation and incubation times, inoculum titer, harvesting methods, etc.).

In some embodiments, Vero cells can be transfected with viral RNA from cloned cDNA plasmid encoding an RSV having a cleavage-resistant G-protein. The transfected Vero cells can be incubated with the viral RNA, and resulting RSV harvested.

In certain embodiments, the method for amplifying an RSV includes a purifying step in which harvested RSV is purified. Purification of the harvested RSV can be carried out by any method for virus purification known in the art. In some embodiments, a purification step can remove, for example, added protease inhibitors.

In some embodiments, the Vero cells can be incubated with the RSV having a cleavage-resistant G protein described herein, or viral RNA encoding the same, and incubated together for a period of about 30 min to about 96 h. In certain embodiments, the incubation period can be about 30 min to about 4 h. In another embodiment the incubation period can be about 2 h. In another embodiment, RSV having a cleavage-resistant G protein can be harvested at a time of between about 48 h and about 96 h following the inoculation. In another embodiment, the RSV can be harvested at a time of about 72 h following inoculation.

In certain embodiments, inhibition of RSV G protein cleavage can be accomplished by incubating the cell culture of inoculated Vero cells in the presence of a protease inhibitor, or protease RNA interference (RNAi) by, for example, siRNA, miRNA, and shRNA. RSV G protein cleavage can be inhibited where the RSV's G protein is not cleavage-resistant. By inhibiting RSV G protein cleavage to the 55 kDa form, RSV vaccine production in Vero cells and infectivity of the vaccine can be significantly improved. Wherein the RSV includes a cleavage-resistant G protein as described herein, G protein cleavage can be further inhibited where the cleavage-resistant G protein resists but does not completely inhibit all cleavage. In certain embodiments, protease inhibitors and RNAi can be used simultaneously to reduce or prevent RSV G protein cleavage.

In some embodiments, one or more protease inhibitors can be included in the cell culture medium during the incubation step to inhibit RSV G protein cleavage. Protease inhibitors can be included at concentrations sufficient to inhibit RSV G protein cleavage. One or more protease inhibitors can be used. In certain embodiments, the protease inhibitors can be any protease inhibitors capable of inhibiting cleavage of RSV G protein. In some embodiments, the protease inhibitors can be cathepsin L inhibitors. Any known cathepsin L inhibitor can be used. Examples of cathepsin L inhibitors include but are not limited to: 3-epiursolic acid; 3-(hydroxyimino)oleanolic acid; 3-(hydroxyimino)masticadienoic acid; ALLM; ALLN; biotin-FA-FMK; CAA0225; CA-074; CA-074 Me; Calpain Inhibitor I; Calpain Inhibitor II; Calpain Inhibitor III; Calpain Inhibitor IV; Calpain Inhibitor V; Calpain Inhibitor VI; Calpeptin; Catfish muscle cathepsin inhibitor, Cathepsin inhibitor peptide; Cathepsin Inhibitor 1; Cathepsin L inhibitor, Cathepsin L inhibitor I;

Cathepsin L inhibitor II; Cathepsin L inhibitor III; Cathepsin L inhibitor IV; Cathepsin L inhibitor Katunuma; CLIK148; Cathepsin/subtilisin inhibitor, Chagasin; Chloroketones; Chymostatin; Clitocypin; CTLA-2 alpha; CTLA-2 beta; Cystatins; Disulfiram; E-64; E-64-c; E-64-d; Gallinamide A; Hurpin; KD-1; KGP94; L006235; Leupeptin; L-transepoxy-succinyl-L Leu cylamine; MDL28170; Mu-Phe-hPhe-FMK; N-(1-Napthalenlsulfonyl)-Ile-Trp-aldehyde; N-Acetyl-L-Leucyl-L-Leucyl-L-methional; Napsul-Ile-Trp-CHO (NSITC); Oxocarbazate; Peptidomimetic 2-cyanopyrrolidines; Phenylmethanesulfonyl fluoride; Protein C inhibitor; SID 26681509; Squamous cell carcinoma antigen; Thiocarbazate; Triterpenoids; Z-FA-FMK; Z-FF-FMK; ZINC03846634 (APQ); ZINC08764437 (NFP); Z-Phe-Ala-CHN2; Z-Phe-Phe-CH2F; Z-Phe-Tyr (tBu)-diazomethylketone; Z-Phe-Tyr-aldehyde; α-macroglobulin; a cathepsin L inhibitor of WO 2000049008 A1, which is hereby incorporated by reference in its entirety; and combinations thereof. In some embodiments, the cathepsin L inhibitor is Leupeptin.

In embodiments where RNAi is used to inhibit RSV G protein cleavage, Vero cells can be transfected with a molecule capable of interfering with the RNA of at least one protease involved in RSV G protein cleavage, such as cathepsin L RNA, thereby silencing gene expression and inhibiting cleavage. Molecules capable of interfering with RNA include siRNA, miRNA, and shRNA. In certain embodiments, the molecule is specific for cathepsin L RNA. Methods for silencing gene expression by RNAi are known in the art. Any method known in the art may be used to design and use RNAi molecules to target a protease involved in RSV G protein cleavage (e.g., cathepsin L).

In certain embodiments, RSV amplified by a method described can be formulated into an immunogenic composition against RSV. In some embodiments, the immunogenic composition against RSV can be a pharmaceutical composition, such as a vaccine.

In certain embodiments, an immunogenic composition against RSV can include an RSV harvested following amplification using a method described herein. In some embodiments, the harvested RSV can either have a cleavage-resistant G protein resulting from a mutation described herein, or the majority harvested RSV has a full length G protein relative to cleaved G protein as a result of incubation with a protease inhibitor. In some embodiments, the immunogenic composition against RSV includes a live attenuated RSV. In certain embodiments, the immunogenic composition against RSV can include one or more pharmaceutically acceptable, carriers, vehicles, excipients, or any combination thereof. Suitable pharmaceutical carriers, vehicles, and excipients for formulating a pharmaceutically acceptable immunogenic compound, including vaccines, are known in the art. In some embodiment, the immunogenic compositions can include at least one adjuvant for further induction of the immune system in a subject when administered.

In some embodiments, the immunogenic composition against RSV can have about 4- to about 10-fold greater infectivity than an immunogenic composition against RSV produced using a method in which RSV G protein cleavage was not inhibited. In some embodiments, an immunogenic composition against RSV produced using methods described herein can have about 10-fold greater infectivity.

Certain embodiments provide methods for inducing an effective immune response against RSV in a subject. In some embodiments, the method can include administering an immunologically effective dose of an immunogenic composition against RSV. In some embodiments, the immunogenic composition against RSV includes a live attenuated RSV having a full length G protein. Full length RSV G protein can be achieved in virions grown in Vero cells either by a mutation described herein resulting in a cleavage-resistant RSV G protein, or by producing the RSV in Vero cells in the presence of a protease inhibitor such as a cathepsin L inhibitor. In certain embodiments, the subject can be a human subject. In some embodiments, the subject can be a human infant or child. The immunogenic composition against RSV can be administered to a subject at risk of acquiring an RSV infection, or a subject having an RSV infection, including a subject having a recurrent infection. Accordingly, certain embodiments provide methods of preventing and/or treating an RSV infection comprising administering an immunogenic composition described herein.

In certain embodiments, methods for inducing an effective immune response against RSV can reduce the incidence of, or probability of, recurrent RSV infection in a subject. In other embodiments, an immunogenic composition against RSV can be administered to a patient post-infection, thereby ameliorating the symptoms and/or course of the infection, as well as preventing recurrence. In one embodiment, a subject is administered at least one immunologically effective dose subsequent to an initial dose. The immunogenic composition against RSV can be administered to the subject once, or can be administered a plurality of times, e.g., one, two, three, four, or five times.

In some embodiments, immunogenic compositions against RSVs can be administered to a subject in a convenient manner, for example, subcutaneous, intravenous, by oral administration, inhalation, intradermal, transdermal application, intravaginal application, topical application, intranasal or rectal administration. In one embodiment, an immunologically effective dose of an immunogenic composition against RSV can be administered to a human infant intranasally. In other embodiments, the route of administration can be intradermal administration or oral administration.

In certain embodiments, an immunogenic composition can be administered to a subject in an appropriate pharmaceutically acceptable carrier or diluent, co-administered with enzyme inhibitors or in an appropriate carrier such as liposomes. As used herein, the term "pharmaceutically acceptable carrier" includes diluents such as saline and aqueous buffer solutions. Dispersions can also be prepared in glycerol, liquid polyethylene glycols, and mixtures thereof and in oils. Under ordinary conditions of storage and use, these preparations may contain a preservative to prevent the growth of microorganisms or other stabilizing formulation (e.g. FTA).

Pharmaceutical compositions suitable for injectable use can be administered by means known in the art. For example, sterile aqueous solutions (where water soluble) or dispersions and sterile powders for the extemporaneous preparation of sterile injectable solutions or dispersion can be used. In all cases, the composition can be sterile and can be fluid to the extent that easy syringability exists. It can be stable under the conditions of manufacture and storage and can be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of microorganisms can be achieved by heating, exposing the agent to detergent, irradiation or adding various antibacterial or antifungal agents.

Sterile injectable solutions can be prepared by incorporating active compound (e.g. a compound that induces an immune response to RSV) in the required amount in an appropriate solvent with one or a combination of ingredients enumerated above, as required, followed by filtered sterilization.

Upon formulation, solutions will be administered in a manner compatible with the dosage formulation and in such amount as is immunologically effective. The formulations are easily administered in a variety of dosage forms, such as the type of injectable solutions described above. It is contemplated that compositions are especially suitable for intramuscular, subcutaneous, intradermal, intranasal and intraperitoneal administration.

In another embodiment, nasal solutions or sprays, aerosols or inhalants can be used to deliver the immunogenic composition of interest. Additional formulations that are suitable for other modes of administration include suppositories and pessaries.

Certain formulations can include excipients, for example, pharmaceutical grades of mannitol, lactose, starch, magnesium stearate, sodium saccharine, cellulose, magnesium carbonate and the like.

A pharmaceutical composition can be prepared with carriers that protect active ingredients against rapid elimination from the body, such as time-release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others are known.

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this disclosure, and without departing from the spirit and scope thereof, can make various changes and modifications to adapt it to various usages and conditions.

Example 1—Protease Cleavage of RSV G Protein by Cathepsin L

Identification of RSV G Protein-Cleaving Protease with Inhibitors.

To elucidate the class of protease responsible for G protein cleavage in Vero cells, cells were treated with increasing concentrations of protease inhibitors after inoculating with recombinant green fluorescent protein expressing RSV (rgRSV). Cells were incubated with rgRSV for 2 h with tipping at 37° C. before replacing inoculum with fresh cell culture medium. Drugs were added at different times post infection. In each case, uninfected, no drug, and vehicle (at the highest concentration used) were included in all experiments as controls. In all experiments at 24 hpi, cell surface proteins were biotinylated, cells lysed and equivalent amounts of protein from each sample were mixed with streptavidin beads. Proteins were displayed by SDS-PAGE, blotted and probed with mAb L9 to the G protein.

Aprotinin, a serine protease inhibitor, leupeptin, a serine/cysteine protease inhibitor; or E-64, a cysteine protease inhibitor were added to the cell culture media (3.125 to 50 μg/ml) from 2-24 hpi. The most likely proteins to be incorporated into the virions are cell surface proteins, so the cell surfaced was biotinylated, proteins isolated from lysed cells with streptavidin beads, and immunobloted with L9, a mAb to the G protein, as a probe (FIG. 1A). In the untreated and vehicle treated samples most of the cell surface G protein was cleaved (~55 kDa), leaving only a small portion of full length (~90 kDa) G protein. Aprotinin treatment (3.125 to 50 μg/ml) did not prevent G protein cleavage. However, both leupeptin and E64 (6.24 to 100 μg/ml) did, in a dose dependent manner. Since both leupeptin and E64 block the activity of cysteine proteases, the protease responsible for cleavage of the G protein in Vero cells is a cysteine protease.

Figure 1B:
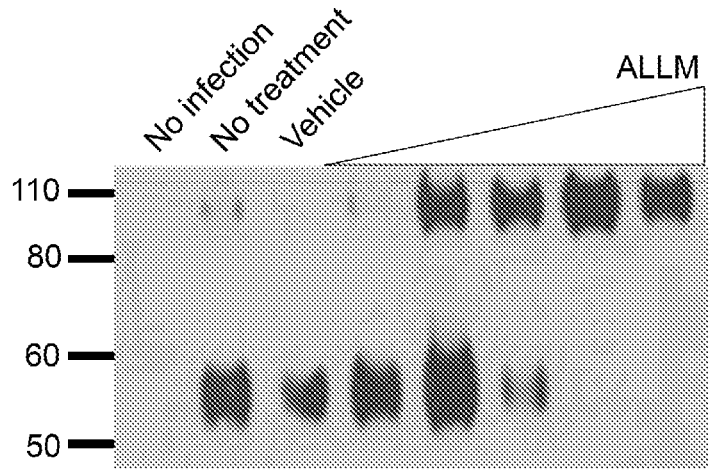
FIG. 1B is an immunoblot representing prevention of cleavage of RSV G protein in the presence of the cathepsin/calpain protease inhibitor ALLM.

To narrow the field of cysteine proteases, cells were treated at 6 hpi with a more specific cysteine protease inhibitor, ALLM (0.1 to 100 μM). While nearly all of the G protein produced in Vero cells was again cleaved in the absence of the inhibitor, ALLM inhibited G protein cleavage (FIG. 1B). Cleavage inhibition by ALLM showed that the cysteine protease responsible for cleaving the RSV G protein in Vero cells is one of four proteases: cathepsin B, cathepsin L, calpain I, or calpain II.

Calpains, exclusively cytoplasmic proteases, are unlikely to be responsible for cleavage because the protein is cleaved C-terminal to its transmembrane domain, the area of the protein that is not exposed to the cytoplasm. Cathepsins B and L reside inside vesicles and organelles, or are secreted from cells, thus having access to the G protein.

Figure 1C:
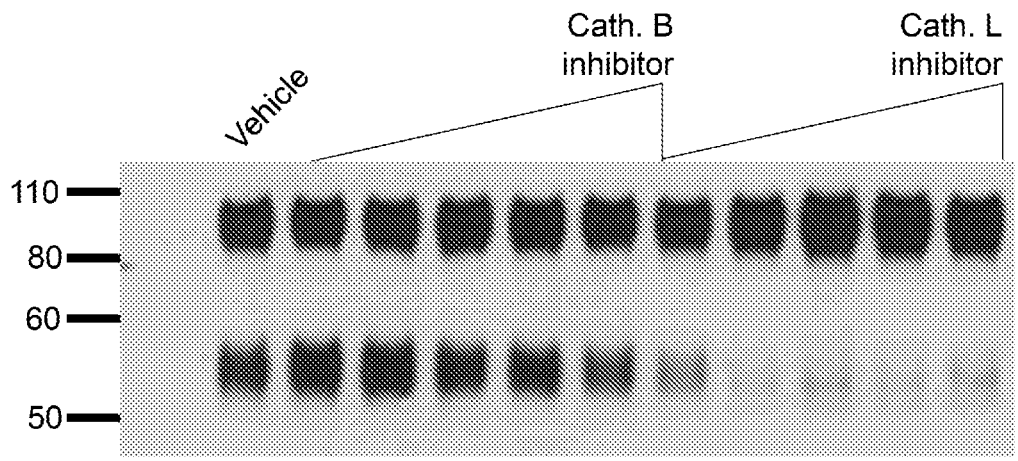
FIG. 1C is an immunoblot representing RSV G protein cleavage in the presence of the selective cathepsin B inhibitor CA-074. The immunoblot also illustrates prevention of cleavage of RSV G protein in the presence of the selective cathepsin L inhibitor III.

RSV-infected HeLa and Vero cells were treated with a cathepsin B inhibitor, CA-074 (0.1 to 100 μM), or a cathepsin L inhibitor, cathepsin L inhibitor III (0.1 to 100 μM) 6 hpi. Cells treated with vehicle produced a mixture of cleaved and uncleaved G protein and the cathepsin B inhibitor did not change this pattern (FIG. 1C). However, cathepsin L inhibition almost completely prevented G protein cleavage, showing that cathepsin L is the protease that cleaves the G protein.

Cathepsin Expression and Activity.

Figure 2A:
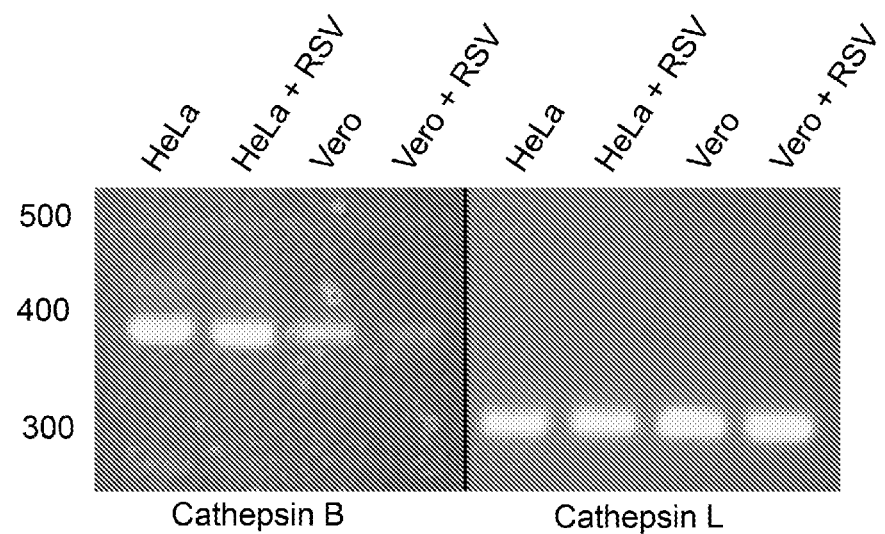
FIG. 2A is an ethidium bromide stained agarose gel of PCR product DNA illustrating cathepsin B and L mRNA expression in both Vero and HeLa cells.
Figure 2B:
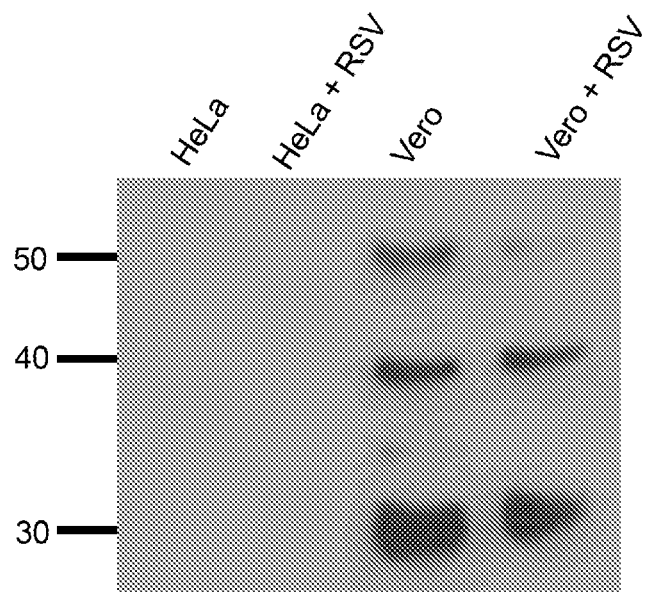
FIG. 2B is a blot illustrating cathepsin L protein expression in Vero cells but not in HeLa cells.

RSV G protein cleavage occurs in many different cell lines, but not as efficiently as in Vero. The expression of cathepsin B and L mRNAs in Vero and HeLa cells was examined by RT-PCR. mRNA for cathepsin B and L was found in both cell types (FIG. 2A). Cells were inoculated with rgRSV or mock inoculated for 2 hours (h), at which time the inoculum was replaced with fresh medium. 24 h post inoculation (hpi) total RNA was extracted and reverse transcribed using random primers. Resulting cathepsin L or B cDNA was amplified and displayed by 2% agarose gel. The mock or rgRSV inoculated cells lysates were then probed with a cathepsin L antibody. Cathepsin L protein was readily detected in Vero but not in HeLa cells (FIG. 2B). Cells were inoculated with rgRSV or mock inoculated for 2 h, at which time the inoculum was replaced with fresh medium. 24 hpi cells were lysed, displayed by SDS-PAGE, blotted and probed with a polyclonal antibody to cathepsin L.

Figure 2C:
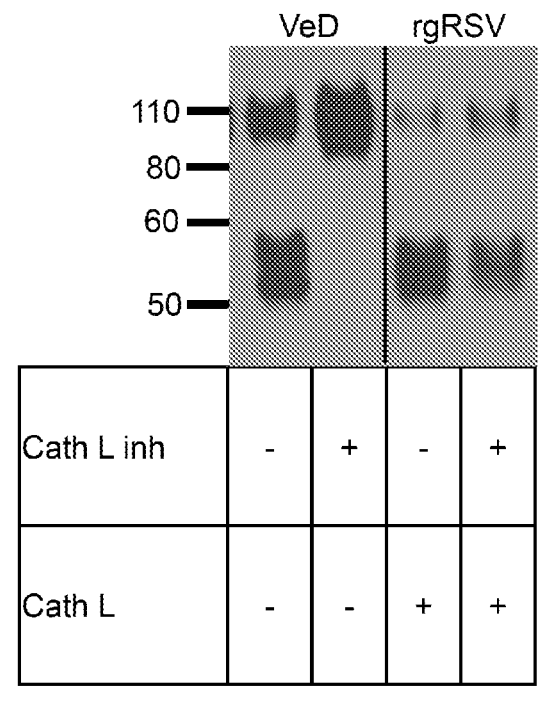

To verify that cathepsin L is sufficient to cleave the G protein, rgRSV was grown in Vero cells in the presence of cathepsin L inhibitor or vehicle. Viruses were harvested and pelleted through a 35% sucrose cushion to separate them from cathepsin L inhibitor. Viruses were resuspended in buffer with pH5.5 and treated with cathepsin L or vehicle. When assayed by immunoblot the G protein in the virus is cleaved in Vero, but cleavage is prevented by cathepsin L inhibition (FIG. 2C). Vero cells were inoculated with rgRSV or mock inoculated for 2 h, at which time the inoculum was replaced with fresh medium. Vero cells were treated with medium containing 0.5 µM cathepsin L inhibitor III at 7 hpi. 72 hpi the medium was harvested and virus was pelleted through a 35% sucrose cushion. The pelleted Vero-derived (VeD) virus was resuspended in buffer (pH5.5) containing 50 ng/d cathepsin L or vehicle. When incubated with cathepsin L after growth, the virus that was grown in the presence of a cathepsin L inhibitor contained a cleaved G protein, again demonstrating that cathepsin L is the protease responsible for G protein cleavage.

Figure 3A:
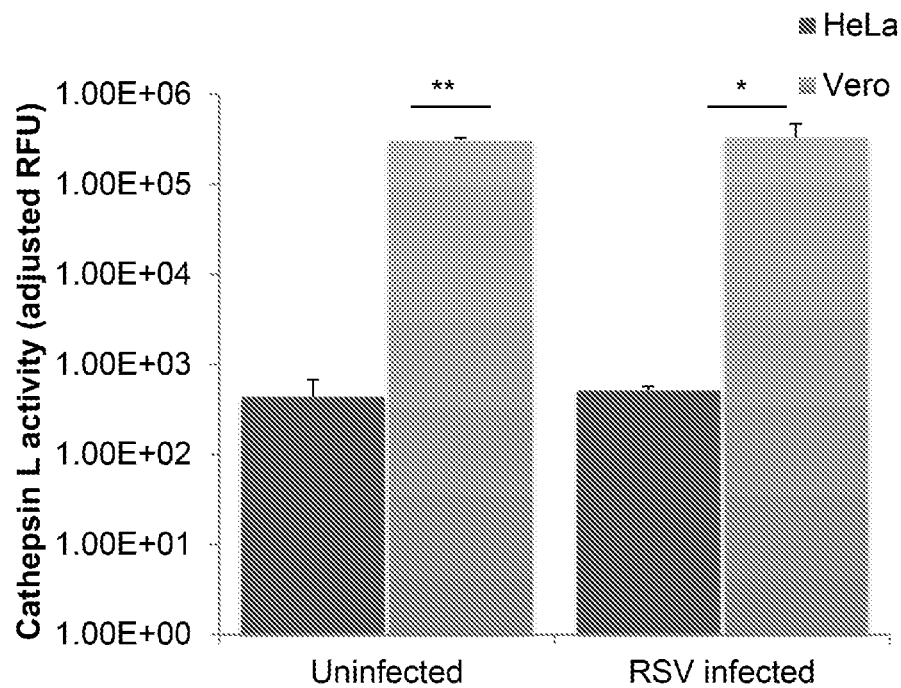
FIG. 3A is a bar graph illustrating higher cathepsin L activity in Vero cells than in HeLa cells, regardless of infection status.
Figure 3B:
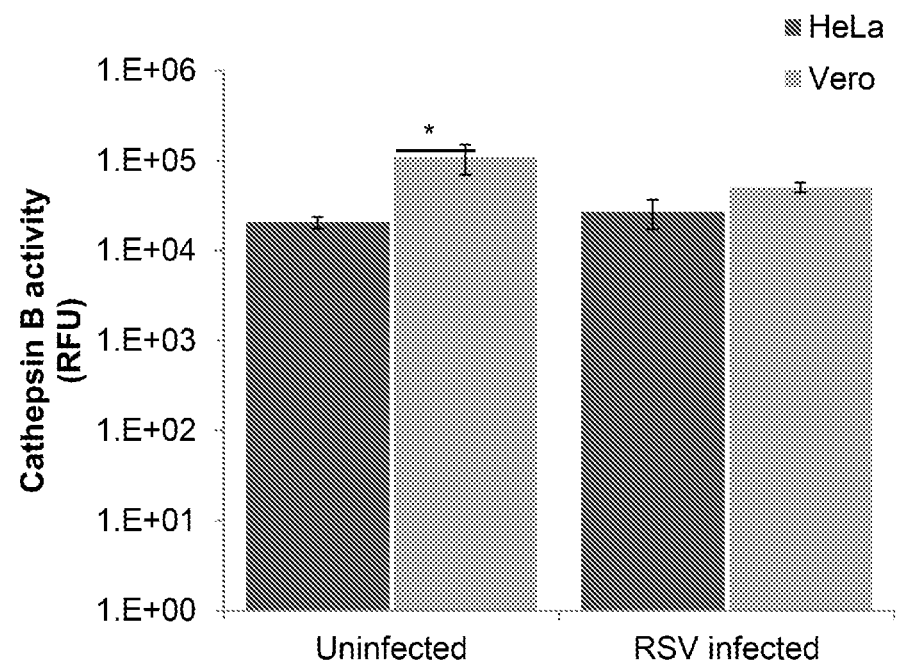
FIG. 3B is a bar graph representing equal cathepsin B activity in infected HeLa and Vero cells.

To compare the activity of the cathepsin L protease in Vero and HeLa, mock or rgRSV inoculated cells were harvested at 24 hpi in the absence of protease inhibitors. The cathepsin L activity in Vero cells was 100-fold greater than in HeLa cells (FIG. 3A). Cells inoculated with rgRSV were harvested without protease inhibitor at 24 hpi. Equal amounts of protein were processed in a cathepsin L assay. *p<0.05, **p<0.001 (unpaired, 2-tailed t-test). Data are representative of three independent experiments. The correlation between cathepsin L activity and the efficiency of G protein cleavage in Vero compared to HeLa cells showed that cathepsin L was the protease responsible for cleaving the G protein. A comparable cathepsin B assay found equal cathepsin B activity in infected HeLa and Vero cells (FIG. 3B). Uninfected cells and cells inoculated with rgRSV were harvested without protease inhibitor at 24 hpi. Equal amounts of protein were processed in a cathepsin B assay. *p<0.05 (unpaired, 2-tailed t-test). Data are representative of three independent experiments.

Cellular Location of Cleavage.

Figures 4A, 4B, 4C:
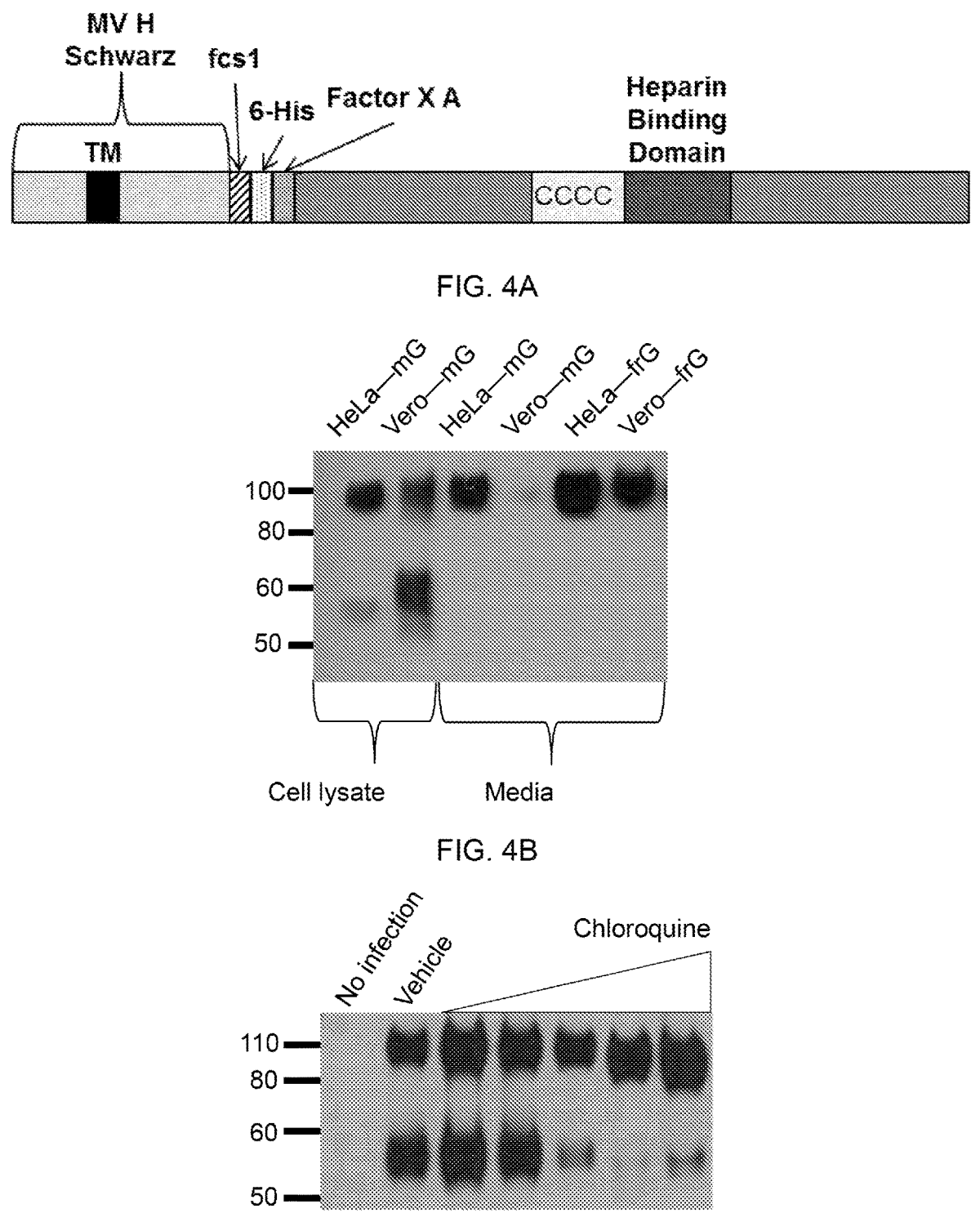

Cathepsin L is found in the nucleus and lysosomes, and can be secreted. To address the cellular location of G protein cleavage in Vero cells, a gene that expresses a furin released version of the G protein, frG, was constructed. In this construct, the G protein transmembrane and cytoplasmic domain was replaced with the measles virus stalk, separated from the ectodomain of the RSV G protein by a furin cleavage site, a 6-His tag, and Factor XA protease sites (FIG. 4A). If full-length G protein is cleaved during its transit to or at the Vero cell surface, the frG protein released into the medium from Vero cells would also be cleaved.

HeLa and Vero cells were transfected with a plasmid expressing the wild-type, membrane-bound G protein (mG), or the frG protein. At 48 h post transfection the cell culture medium was collected and concentrated, and cells were lysed. Total cell lysate, but not concentrated cell medium, was assayed for protein concentration. Concentrated medium or equal amounts of protein from lysate were analyzed by immunoblot. The medium from both cell types contained only intact frG protein (FIG. 4B), indicating that the frG protein was not cleaved during its transit to the Vero cell surface, or in the medium after secretion. For generating FIG. 4B, plasmids expressing membrane bound G protein (mG) or furin-released G protein (frG) were transfected into HeLa or Vero cells. 48 h post transfection cell medium was collected and concentrated. Cells were lysed and equal amounts of protein were displayed by SDS-PAGE gel.

Cathepsin L is a protease present primarily in the interior of the lysosome and is optimally active at acidic pH. Vero cells expressing the G protein were treated with chloroquine to raise the pH of the lysosome. As before, G protein on the cell surface of vehicle-treated Vero cells was a mix of cleaved and uncleaved proteins whereas the G protein on the surface of chloroquine treated cells was primarily full length G protein (FIG. 4C). This inhibition of cleavage by chloroquine showed that cleavage of the G protein occurs within an acidic compartment in the cell, such as the lysosome. To generate FIG. 4C, cells were inoculated with RSV or mock inoculated. 6 hpi the cells were treated with increasing concentrations of chloroquine. 24 hpi cells were biotinylated and G protein assayed Viral Infection of HAE Cultures.

Figure 5A:
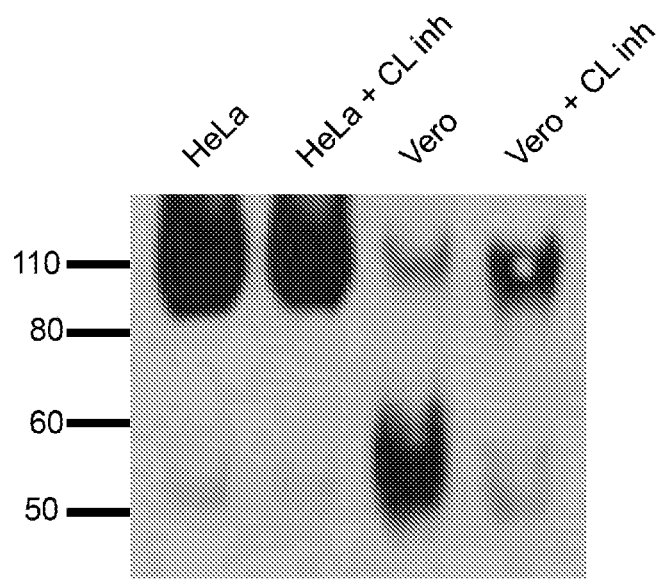
FIG. 5A is an immunoblot illustrating migration of HeLa or Vero derived viral G protein produced in the presence of cathepsin L inhibitor.

As described above, cathepsin L was shown to be the protease that cleaves the G protein in Vero cells and that cleavage takes place during endocytic recycling. To show that inhibition of G protein cleavage in infected cells will result in a virus that is better able to enter HAE cultures, rgRSV was produced in HeLa or Vero cells treated with cathepsin L inhibitor III beginning at 8 hpi. At 72 hpi the medium was collected and virus pelleted through a 35% sucrose cushion to partially purify and concentrate it. The virus pellet was resuspended and half was further purified by linear sucrose density gradient. The G protein from these purified virions was analyzed by immunoblot. The G protein from HeLa cell virions migrated at 90 kDa and was not affected by the inhibitor (FIG. 5A). The G protein from Vero cell virions migrated primarily at 55 kDa but converted to 90 kDa when grown in the presence of the inhibitor. FIG. 5A was generated by inoculating HeLa or Vero cells for 2 h and treating them with cathepsin L inhibitor or DMSO beginning at 8 hpi. 48-72 hpi virus was collected and partially purified by pelleting through a 35% sucrose cushion and displayed by SDS-PAGE, blotted and probed by a mAb to the G protein.

Figure 5B:
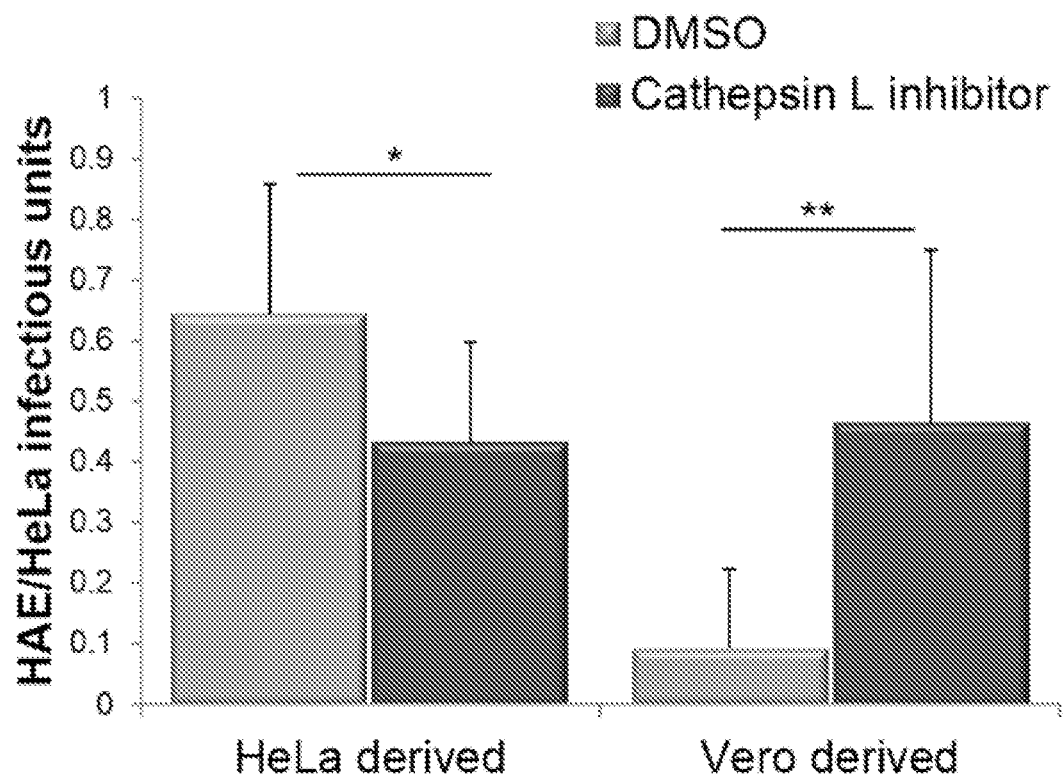
FIG. 5B is a bar graph illustrating treatment of HeLa or Vero cells with a cathepsin L inhibitor during viral production increasing the ability of Vero-derived virus to infect HAE cells.

The remaining virus that had been partially purified through the 35% sucrose cushion was titrated on HeLa cells. Equivalent amounts of infectious virus, determined on HeLa cells, were used to inoculate HAE cultures. While cathepsin L inhibitor had little, if any, effect on the ability of HeLa grown virus to infect HAE cultures, it increased the ability of Vero-grown virus to infect HAE cells by 7-fold (FIG. 5B). For FIG. 5B, equivalent amount of infectious virus, determined by titration on HeLa cells, was used to inoculate HAE cultures. 48 hpi green cells were counted. *p<0.0001 (unpaired, 2-tailed t-test). These results show that that inhibition of G protein cleavage in Vero cells during virus production results in RSV that is able to infect HAE cultures much more efficiently.

Example 2—Identification of RSV G Protein Cleavage Site

G protein mutagenesis to locate the cleavage site. To estimate the position of cleavage, the 4 N-linked glycans in the strain A2 G protein were considered, and NetOGlyc software (Julenius et al., Glycobiology (2005) 15:153-164) was used to identify the most likely positions of the many O-linked sugar sites. It was predicted that the G protein is cleaved in Vero cells around amino acid 210. To confirm our estimate, we mutated the codon at amino acid 211 to a stop codon. The size of this truncated G protein in HeLa cells was determined by transient expression and immunoblot to be between 50 and 60 kDa (FIG. 6A), similar to the position of the 55 kDa G protein in Vero cells. For FIG. 6A, mutated G protein gene was transiently expressed in HeLa cells. 24 h post-transfection cells were harvested, lysed and proteins were separated by SDS-PAGE, blotted and probed with mAb to the G protein.

The G gene in the region of amino acid 210 was modified by deleting stretches of amino acids in this region (200-211, 204-213, 206-215, 208-217, or 209-213). When transiently expressed in Vero and assessed by immunoblot (FIG. 6B), all of these deletion mutants were cleaved less efficiently than the wt G protein. Most of the mutants almost completely ablate cleavage. They all share amino acids 208-211. However, A206-210 and A206-215, both of which bring together amino acids that can also serve as a cathepsin L cleavage site. For FIG. 6B, the mutated G protein genes were transiently expressed in Vero cells. 24 h post-transfection cells were harvested, lysed and proteins were separated by SDS-PAGE, blotted and probed with mAb to the G protein. These data show that amino acids 208-211 are important for cleavage.

To identify which amino acids are important for cleavage, individual amino acids in and around this region were changed to alanine. These mutant G proteins were transiently expressed in Vero cells and assessed by immunoblot (FIG. 6C). For FIG. 6C, the mutated G protein genes were transiently expressed in Vero cells. 24 hours post-transfection cells were harvested, lysed and proteins were separated by SDS-PAGE, blotted and probed with mAb to the G protein. Alanine substitutions at L208, K209, K212, and D214 were partially to nearly completely resistant to cleavage, and showed that the three C-terminal amino acids also play a role. Alanine substitution for L208 was the most efficient and K209 was the second most efficient at inhibiting cleavage, showing that these amino acids are critical for protease recognition.

Example 3—the Cleavage-Resistant RSV G Protein Mutant L208A

Virus Containing a Cleavage-Resistant G Protein.

Figure 7A:
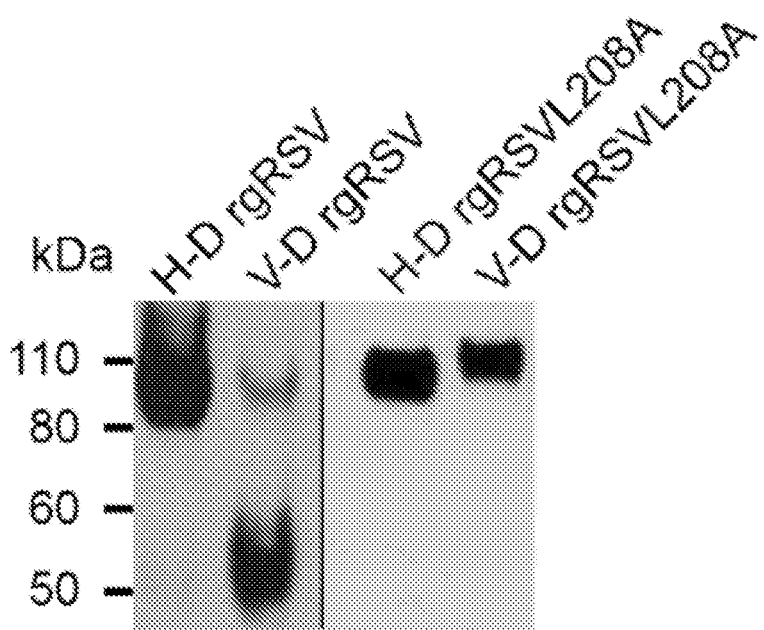
FIG. 7A is an immunoblot illustrating the prevention of G protein cleavage by the L208A mutation in RSV virions.
Figure 7B:
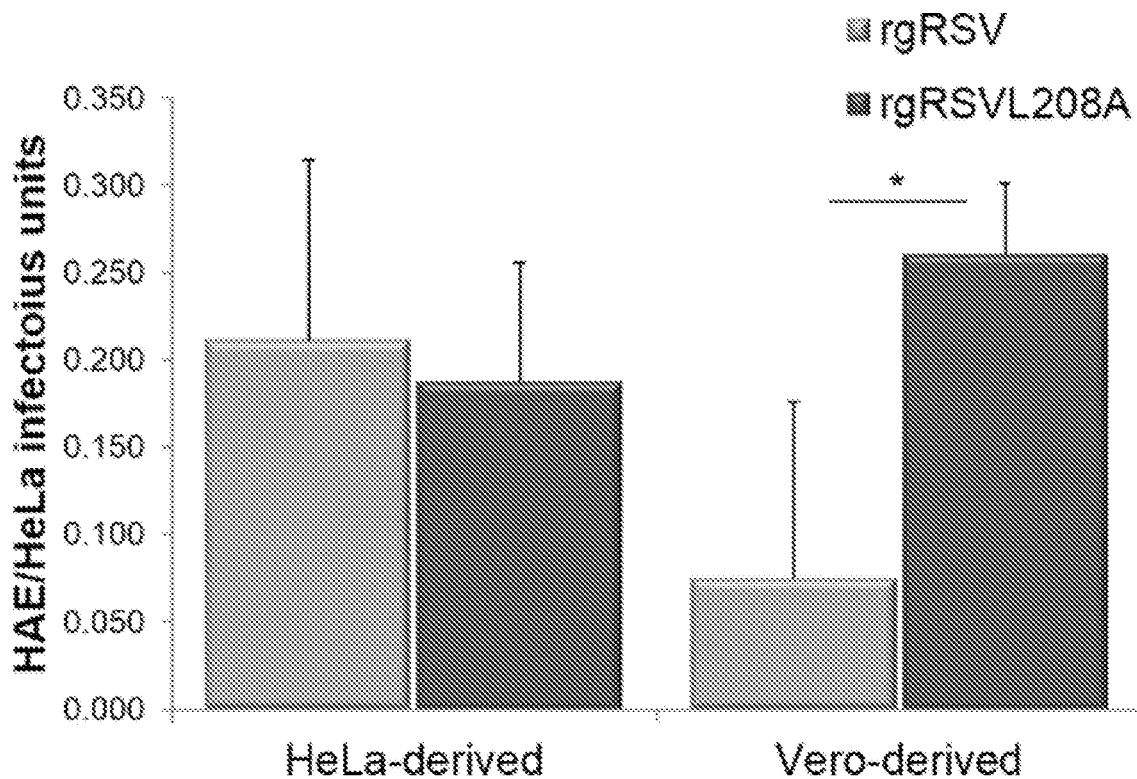
FIG. 7B is a bar graph illustrating increased infectivity for HAE cultures of G mutant virus rgRSVL208A grown in Vero cells.

To test the infectivity of Vero-derived virus with an uncleavable G in HAE cultures, the L208A mutation was incorporated into the whole virus. rgRSV and rgRSV-L208A were grown in HeLa or Vero cells, purified by sucrose gradient, and their virion G proteins assessed by immunoblot (FIG. 7A). For FIG. 7A, the L208A mutant G protein gene was inserted into the full-length RSV genome cDNA, in place of the wt G protein. The mutant RSV was rescued and grown in HeLa or Vero cells, purified by centrifugation through a 35% sucrose cushion, and G protein assessed as before. Vero-grown rgRSV-L208A virions contained uncleaved G protein. The viruses were titrated on HeLa cells and equivalent infectious units used to inoculate HeLa or HAE cultures. Infected cells were counted and data displayed as the ratio of HAE to HeLa infectious units (FIG. 7B). For FIG. 7B, virus was titrated on HeLa cells and equivalent infectious units were used to inoculate HAE and HeLa in parallel. Virus-infected (green) cells were counted at 24 (HeLa) or 48 (HAE) hpi. Data is displayed as infectious units on HAE divided by the average of infectious units on HeLa assayed on the same day. Data from multiple experiments were pooled. *$p<0.05$ **$p<1\times10^{-8}$ (unpaired, 2-tailed t-test). rgRSV-L208A grown in Vero cells was significantly more infectious for HAE cultures than rgRSV grown in Vero cells.

Example 4—Materials and Methods

Cell Culture.

HeLa and Vero cells were cultured in DMEM (Corning Incorporated, Corning, N.Y.) supplemented with 10% FBS (Atlanta Biologicals, Norcross, Ga.), 1 mM HEPES (GE Healthcare Life Sciences, Logan, Utah), and 2 mM Glutamax (Life Technologies, Carlsbad, Calif.). Cells were incubated at 37° C. and 5% CO2.

Primary, well-differentiated human airway epithelial (HAE) cultures were generated from human airway tissue (Fulcher et al., Methods Mol Med (2005) 107:183-206). For infection experiments they were grown on collagen coated Trans-well inserts (Corning Incorporated). Upon reaching confluency and forming tight junctions, the apical medium was removed and cultures were maintained at an air-liquid interface for 6 to 8 weeks to form well-differentiated, polarized cultures. Basal medium was changed three times weekly and the apical surface was washed for 2 h once weekly with D-PBS.

Mutant Virus Rescue.

The full-length RSV cDNA construct, RW30 (Kwilas et al., J Virol (2010) 84:7770-7781), was used as the backbone for a modification of the G protein gene at amino acid 208 from a lysine to an alanine. RW30 was digested with restriction enzymes EcoICRI and SacII (Thermo Fisher Scientific Waltham, Mass.) to remove the G gene, and the remaining vector was isolated from an 0.5% agarose gel following electrophoresis and eluted from the gel fragment with the Qiaex II gel elution kit (Qiagen, Valencia, Calif.). The G protein gene was replaced with a synthetic double-stranded DNA gBlock (Integrated DNA Technologies, Coralville, Iowa) containing an unrelated gene, the red fluorescent protein gene, using the Gibson Assembly kit (New England Biolabs, Ipswich, Mass.). DH10-beta competent *E. coli* high efficiency cells (New England Biolabs) were transformed and plasmid containing bacteria were selected on agar plates with tetracycline (10 μg/ml) at 30° C. Colonies were screened with PCR supermix (Life Technologies) using primers against the G protein. Colonies containing the correct plasmid sequence were grown in 1×LB containing tetracycline (10 μg/ml) in a 30° C. incubator shaking at 150 rpm. Plasmids were isolated using the HiSpeed plasmid maxi kit (Qiagen). A second round of mutagenesis, selection, and isolation was used to replace the red fluorescent protein with a mutant G protein gene with an alanine at position 208. G protein mutant virus, rgRSVL208A, was rescued from this plasmid (Collins et al., PNAS (1995) 92:11563-11567).

Virus Growth.

HeLa or Vero cells were inoculated with recombinant green fluorescent protein (GFP)-expressing recombinant RSV (rgRSV), strain D53 (derived from strain A2), or rgRSVL208A in medium supplemented as described above. At 2 h post inoculation (hpi) the inoculum was replaced with fresh medium. At 48 hpi medium was renewed and at 72 hpi viruses cells were scraped, medium was collected and pulse vortexed. Cells were pelleted at 1200×g for 5 min in a Megafuge (Baxter Scientific Products) and supernatant was aliquoted, snap frozen on dry ice, and stored at −80° C. All viruses were titrated on HeLa cells.

The effect of protease inhibitors on the infectivity of RSV produced by Vero and HeLa cells was tested by inoculating cells and 2 hpi media was changed. At 7 hpi medium containing 0.5 CpM cathepsin L inhibitor III (Calbiochem, San Diego, Calif.) or an equal volume of the vehicle, DMSO was added to the cells. 72 hpi virus was harvested as described above, but instead of aliquoting and snap freezing, 15 ml of virus-containing medium was layered on top of 15 ml of 35% sucrose cushion in 1× Hanks Balanced Salt Solution, with calcium and magnesium, and centrifuged overnight at 4° C. and 26,000×g in an F14-14×50cy rotor for Sorvall Lynx 6000 (Thermo Fisher) to remove the drug and partially purify the virus. A portion of these virus preparations was further purified through a sucrose gradient by centrifugation in an SW41 rotor and Beckman Ultracentrifuge at 40,000 rpm for 20 h. Gradient fractions were separated by SDS-PAGE (see below) and those containing virions were identified by immunoblot stained with a mAb to the N protein (Walsh et al., J Gen Virol (1989) 70(11): 2953-2961). Fractions containing virus were separated by SDS-PAGE and G protein detected by immunoblot using a mAb, L9 (Edward Walsh, University of Rochester).

Cathepsin L Treatment.

Viruses grown in the presence of vehicle or cathepsin L inhibitor were pelleted through sucrose cushion as described above. Virus was resuspended in citric acid-sodium phosphate buffer at pH5.5. Active cathepsin L enzyme or vehicle was added to a final concentration of 50 ng/μl. Samples were incubated for 2 h at 37° C. and the G protein was assayed by immunoblot.

Virus Infection and Drug Treatment.

HeLa and Vero cells were rgRSV (MOI: 1) or mock inoculated. 2 hpi the inoculum was replaced with fresh complete medium, and 4 hpi cells the medium was changed again to complete medium with 2-fold dilutions of these protease inhibitors (Sigma-Aldrich, St. Louis, Mo.), dissolved in water: Aprotinin (3.125 to 50 μg/ml); Leupeptin (6.25 to 100 μg/ml); E-64 (6.25 to 100 μg/ml); or equal volumes of water in medium. In other experiments, cells were treated at 6 hpi with: 10-fold dilutions (0.1 to 100 μM) of: Cathepsin inhibitor I (Calbiochem); ALLM (Santa Cruz, Dallas, Tex.); Chloroquine diphosphate salt (Sigma Aldrich) or equivalent volumes of vehicle (water); CA-074 (Calbiochem); Cathepsin L inhibitor III (Calbiochem); or an equal volume of vehicle (DMSO) in medium.

Biotinylation and Immunoblot Analysis.

At 24 hpi cells were biotinylated with Ez-link Sulfo-NHS-LC-Biotin (Thermo Fisher). Cells were lysed with lysis buffer containing 150 mM NaCl, 1% Triton X-100, 50 mM Tris, 0.1% SDS, and 1× Halt protease cocktail inhibitor (Thermo Fisher). Proteins were quantified using BCA protein assay kit (Pierce, Waltham, Mass.), and equal amounts of protein were added to high capacity streptavidin agarose beads (Thermo Fisher). The mixtures were rotated for 1 h at 4° C., the beads were pelleted and washed with lysis buffer (without protease cocktail inhibitor), NuPage LDS sample buffer was added, and boiled for 5 min, separated by NuPAGE Novex 4-12% bis-tris protein gels and transferred to nitrocellulose in an iBlot transfer stack, using the iBlot transferring system (Life Technologies) for immunoblot analysis. Blots were probed with mouse monoclonal L9, D14 (Ed Walsh, University of Rochester) or a polyclonal rabbit Anti-CTSL antibody (Sigma) followed by the appropriate human serum-adsorbed and peroxidase labeled secondary antibody: anti-mouse IgG (H+L) antibody or anti-rabbit IgG (H+L) antibody (KPL, Inc. Gaithersburg, Md.).

PCR.

Primers against cathepsin B and L were designed to cross exon-exon boundaries to decrease the chance of amplifying genomic DNA (Cathepsin B Forward: gggacggctgtaatgg (SEQ ID NO: 2), Reverse: ttggtacactcctgacttg (SEQ ID NO: 3); Cathepsin L Forward: gaggcaacagaagaatcc (SEQ ID NO: 4), Reverse: cccagctgttcttcacc (SEQ ID NO: 5)). Total mRNA was isolated from uninfected cells at 24 hpi, reverse transcribed (with and without reverse transcriptase), and amplified by PCR. PCR products were separated by 2% agarose gels and visualized with EtBr.

Cathepsin Activity Assays.

At 24 hpi, inoculated or mock infected cells were treated with lysis buffer without protease inhibitors and maintained on ice. Protein concentrations were determined with a BCA protein assay (Pierce) and 6.25 ng of Vero cell protein or 50 ng of HeLa cell protein were assayed by the InnoZyme Cathepsin L activity kit, Fluorogenic (Calbiochem). Results were normalized for protein added to yield the relative fluorescence intensity (RFU). 25 ng protein from HeLa or Vero was similarly assayed using InnoZyme Cathepsin B activity kit, Fluorogenic (Calbiochem).

Mutagenesis.

A soluble version of the A2 strain G protein was constructed by replacing its cytoplasmic tail and transmembrane domain with the Schwarz Measles Virus cytoplasmic tail, transmembrane domain and a portion of the stalk and inserting a furin cleavage site, 6-His tag and Factor XA site between the MV stalk and the G protein. The furin-released G (frG) protein is processed as a membrane bound protein but released from the membrane by furin during transit through the Golgi.

The strain A2 G protein plasmid was mutagenized using synthetic double strand gBlock DNA (Integrated DNA Technologies). Van91I (Thermo Fisher) and Xho I (New England Biolabs) were used to digest plasmid and gBlock. Doubly-digested plasmid was isolated by agarose gel electrophoresis. Digested gBlock and eluted plasmid DNAs were ligated with T4 DNA ligase (Promega, Madison, Wis.), and transformed into One Shot MachI-T1 chemically competent bacteria (Life Technologies). Plasmids were extracted using HiSpeed or Plasmid Plus Maxi kits (Qiagen).

Transfection.

Wild type G or frG proteins were expressed in HeLa or Vero cells following plasmid transfection with FuGene HD (Promega) or Lipofectamine LTX (Life Technologies), respectively, in medium containing 2% FBS. In frG experiments, medium was collected and concentrated using Ultra-cel-10 K centrifugal filters (EMD Millipore, Billerica, Mass.). For other transfection experiments, Vero cells were transfected using Lipofectamine 3000 (Life Technologies) in medium containing 10% FBS. For all transfection experiments, cells were lysed and protein quantified by BCA assay. Equivalent HeLa or Vero cell lysate protein and equivalent volumes of concentrated proteins from the medium were analyzed by immunoblotting.

HAE Viral Infections.

The apical surface of well-differentiated HAE cultures in Trans-wells was washed with DPBS for 2 h and the basal medium changed before equivalent pfu (titrated in HeLa cells), between 2,000 and 10,000 pfu, depending on the HAE culture source, were diluted in HAE medium and added to the apical chamber of the Trans-well. In parallel, HeLa cells were inoculated with 200 pfu. At 2 hpi the inocula were removed, and replaced with fresh medium only on HeLa cells. Fluorescent (green) cells were visualized with an EVOS fl inverted fluorescence microscope (Life Technologies) and counted in HeLa cultures at 24 hpi and on HAE cultures at 48 hpi. Three or more experiments were pooled and analyzed together.

Statistical Analysis.

A 2-tailed t-test was performed on each pair (HeLa derived versus Vero derived). $p<0.05$ was considered significant.

All of the compositions and methods disclosed and claimed herein can be made and executed without undue experimentation in light of the present disclosure. While the compositions and methods have been described in terms of particular embodiments, it is apparent to those of skill in the art that variations maybe applied to the compositions and methods and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. A method for producing an immunogenic composition against respiratory syncytial virus (RSV) comprising:
   providing a Vero host cell culture;
   inoculating the Vero host cell culture with an RSV comprising a mutated attachment (G) protein having an amino acid substitution at one or more amino acids selected from: L208; K209; K212; K213; and D214 of the attachment protein represented by SEQ ID NO: 1, wherein the RSV is attenuated;
   incubating the Vero host cell culture with the RSV;
   harvesting RSV following the incubation step; and
   formulating the harvested RSV into an immunogenic composition against RSV.

2. The method of claim 1, further comprising purifying the harvested RSV.

3. The method of claim 1, wherein the Vero host cell culture is incubated with the RSV for a time period of between about 30 minutes and about 4 hours.

4. The method of claim 1, wherein the RSV is harvested at a time of between 48 and 96 hours following inoculation.

5. The method of claim 1, wherein the formulating step comprises bringing the harvested attenuated RSV into association with a pharmaceutically acceptable carrier, vehicle, or excipient, an adjuvant, or a combination thereof.

6. A method for producing an immunogenic composition against respiratory syncytial virus (RSV) comprising:
   providing a Vero host cell culture;
   inoculating the Vero host cell culture with an RSV strain having a wild-type G protein or a mutated RSV comprising a mutated attachment (G) protein having an amino acid substitution at one or more amino acids selected from: L208; K209; K212; K213; and D214 of the attachment protein represented by SEQ ID NO: 1, wherein the RSV having the wild-type G protein or the mutated RSV of claim 1 is attenuated;
incubating the inoculated Vero host cell culture;
inhibiting Vero cell cathepsin L during the incubating step;

harvesting RSV following the incubation step; and formulating the harvested RSV into an immunogenic composition against RSV.

7. The method of claim 6, further comprising purifying the harvested RSV.

8. The method of claim 6, wherein the formulating step comprises bringing the harvested attenuated RSV into association with a pharmaceutically acceptable carrier, vehicle, or excipient, an adjuvant, or a combination thereof.

9. The method of claim 6, wherein Vero cell cathepsin L is inhibited by incubating the inoculated Vero host cell culture with at least one cathepsin L inhibitor.

10. The method of claim 9, wherein the at least one cathepsin L inhibitor selected from the group consisting of: 3-epiursolic acid; 3-(hydroxyimino)oleanolic acid; 3-(hydroxyimino)masticadienoic acid; ALLM; ALLN; biotin-FA-FMK; CAA0225; CA-074; CA-074 Me; Calpain Inhibitor I; Calpain Inhibitor II; Calpain Inhibitor III; Calpain Inhibitor IV; Calpain Inhibitor V; Calpain Inhibitor VI; Calpeptin; Catfish muscle cathepsin inhibitor; Cathepsin inhibitor peptide; Cathepsin Inhibitor 1; Cathepsin L inhibitor; Cathepsin L inhibitor I; Cathepsin L inhibitor II; Cathepsin L inhibitor III; Cathepsin L inhibitor IV; Cathepsin L inhibitor Katunuma; CLIK148; Cathepsin/subtilisin inhibitor; Chagasin; Chloroketones; Chymostatin; Clitocypin; CTLA-2 alpha; CTLA-2 beta; Cystatins; Disulfiram; E-64; E-64-c; E-64-d; Gallinamide A; Hurpin; KD-1; KGP94; L006235; Leupeptin; L-transepoxysuccinyl-L Leu cylamine; MDL28170; Mu-Phe-hPhe-FMK; N-(1-Napthalenlsulfonyl)-Ile-Trp-aldehyde; N-Acetyl-L-Leucyl-L-Leucyl-L-methional; Napsul-Ile-Trp-CHO (NSITC); Oxocarbazate; Peptidomimetic 2-cyanopyrrolidines; Phenylmethanesulfonyl fluoride; Protein C inhibitor; SID 26681509; Squamous cell carcinoma antigen; Thiocarbazate; Triterpenoids; Z-FA-FMK; Z-FF-FMK; ZINC03846634 (APQ); ZINC08764437 (NFP); Z-Phe-Ala-CHN2; Z-Phe-Phe-CH2F; Z-Phe-Tyr (tBu)-diazomethylketone; Z-Phe-Tyr-aldehyde; a-macroglobulin; and combinations thereof.

11. The method of claim 6, wherein cathepsin L is inhibited by silencing a gene encoding cathepsin L in cells of the host cell culture.

12. The method of claim 11, wherein the gene encoding cathepsin L is silenced by one or more molecules selected from: siRNA; miRNA; shRNA; and combinations thereof.

13. The method of claim 6, wherein the inoculated Vero host cell culture is incubated with the RSV for a time period of between about 30 minutes and about 4 hours.

14. The method of claim 6, wherein the RSV is harvested at a time of between 48 and 96 hours following inoculation.

15. An immunogenic composition against RSV produced by the method of claim 1, wherein the immunogenic composition comprises a pharmaceutically acceptable carrier, vehicle, or excipient, an adjuvant, or a combination thereof.

16. An immunogenic composition against RSV produced by the method of claim 6, wherein the immunogenic composition comprises a pharmaceutically acceptable carrier, vehicle, or excipient, an adjuvant, or combination thereof.

17. A method for inducing an effective immune response against respiratory syncytial virus (RSV) infection in a subject, comprising administering to the subject an immunologically effective dose of the immunogenic composition against RSV of claim 1.

18. The method of claim 17, wherein the subject is human.

19. The method of claim 17, wherein the subject is a human infant or child.

20. The method of claim 17, wherein the immunogenic composition against RSV is administered via an administration route selected from: intranasal administration; subcutaneous administration; intramuscular administration; intradermal administration; and oral administration.

21. The method of claim 17, further comprising administering at least one subsequent immunologically effective dose of the immunogenic composition against RSV.

22. The method of claim 1, further comprising inhibiting Vero cell cathepsin L during the incubating step.

23. The method of claim 22, wherein Vero cell cathepsin L is inhibited by incubating the Vero host cell culture with the attenuated RSV with at least one cathepsin L inhibitor.

24. The method of claim 23, wherein the at least one cathepsin L inhibitor selected from the group consisting of: 3-epiursolic acid; 3-(hydroxyimino)oleanolic acid; 3-(hydroxyimino)masticadienoic acid; ALLM; ALLN; biotin-FA-FMK; CAA0225; CA-074; CA-074 Me; Calpain Inhibitor I; Calpain Inhibitor II; Calpain Inhibitor III; Calpain Inhibitor IV; Calpain Inhibitor V; Calpain Inhibitor VI; Calpeptin; Catfish muscle cathepsin inhibitor; Cathepsin inhibitor peptide; Cathepsin Inhibitor 1; Cathepsin L inhibitor; Cathepsin L inhibitor I; Cathepsin L inhibitor II; Cathepsin L inhibitor III; Cathepsin L inhibitor IV; Cathepsin L inhibitor Katunuma; CLIK148; Cathepsin/subtilisin inhibitor; Chagasin; Chloroketones; Chymostatin; Clitocypin; CTLA-2 alpha; CTLA-2 beta; Cystatins; Disulfiram; E-64; E-64-c; E-64-d; Gallinamide A; Hurpin; KD-1; KGP94; L006235; Leupeptin; L-transepoxysuccinyl-L Leu cylamine; MDL28170; Mu-Phe-hPhe-FMK; N-(1-Napthalenlsulfonyl)-Ile-Trp-aldehyde; N-Acetyl-L-Leucyl-L-Leucyl-L-methional; Napsul-Ile-Trp-CHO (NSITC); Oxocarbazate; Peptidomimetic 2-cyanopyrrolidines; Phenylmethanesulfonyl fluoride; Protein C inhibitor; SID 26681509; Squamous cell carcinoma antigen; Thiocarbazate; Triterpenoids; Z-FA-FMK; Z-FF-FMK; ZINC03846634 (APQ); ZINC08764437 (NFP); Z-Phe-Ala-CHN2; Z-Phe-Phe-CH2F; Z-Phe-Tyr (tBu)-diazomethylketone; Z-Phe-Tyr-aldehyde; a-macroglobulin; and combinations thereof.

25. The method of claim 22, wherein cathepsin L is inhibited by silencing a gene encoding cathepsin L in cells of the host cell culture.

26. The method of claim 25, wherein the gene encoding cathepsin L is silenced by one or more molecules selected from: siRNA; miRNA; shRNA; and combinations thereof.

* * * * *